(12) United States Patent
Dvorak

(10) Patent No.: US 10,717,684 B2
(45) Date of Patent: Jul. 21, 2020

(54) BIOSOLIDS DIGESTER AND PROCESS FOR BIOSOLIDS PRODUCTION

(71) Applicant: DVO Licensing, Inc., Chilton, WI (US)

(72) Inventor: Stephen W. Dvorak, Chilton, WI (US)

(73) Assignee: DVO LICENSING, INC., Chilton, WI (US)

( * ) Notice: Subject to any disclaimer, the term of this patent is extended or adjusted under 35 U.S.C. 154(b) by 264 days.

(21) Appl. No.: 14/482,666

(22) Filed: Sep. 10, 2014

(65) Prior Publication Data

US 2014/0377855 A1 Dec. 25, 2014

Related U.S. Application Data

(62) Division of application No. 13/511,030, filed as application No. PCT/US2010/058012 on Nov. 24, 2010, now Pat. No. 8,835,155.

(Continued)

(51) Int. Cl.
*C05F 17/02* (2006.01)
*C05F 17/921* (2020.01)
(Continued)

(52) U.S. Cl.
CPC ............ *C05F 17/921* (2020.01); *C02F 11/04* (2013.01); *C05F 17/40* (2020.01); *C05F 17/50* (2020.01);
(Continued)

(58) Field of Classification Search
CPC .. C05F 11/04; C05F 17/0018; C05F 17/0027; C05F 17/0217; C12M 21/04; C12M 29/24; C12M 41/12; C12M 41/18; Y02W 10/23; Y02W 30/43; Y02W 30/47; Y02P 20/129; Y02P 20/133; Y02P 20/145
(Continued)

(56) References Cited

U.S. PATENT DOCUMENTS 3,845,939 A 11/1974 Waldenville
4,022,665 A 5/1977 Ghosh et al.
(Continued)

FOREIGN PATENT DOCUMENTS

DE 150881 A1 * 9/1981 .............. C02F 11/12
EP 0213691 A2 3/1987
(Continued)

OTHER PUBLICATIONS

Ivan Boschnakow, "Abstratct English language translation of DD 150881A1", translated on Jun. 9, 2016.*
(Continued)

*Primary Examiner* — Liban M Hassan
(74) *Attorney, Agent, or Firm* — Husch Blackwell LLP

(57) ABSTRACT

The invention relates to methods and apparatuses for producing Class A biosolids. In yet another embodiment, the invention relates to a method comprising digesting waste material by anaerobic digestion, and yielding Class A biosolids. In still yet another embodiment, the invention relates to a system for anaerobic digestion of waste material to produce Class A biosolids. In still yet another embodiment, the invention relates to a system for anaerobic digestion of waste material comprising a mixing chamber, a digester, a heating pit, and an effluent pit.

11 Claims, 19 Drawing Sheets

Related U.S. Application Data

(60) Provisional application No. 61/264,420, filed on Nov. 25, 2009.

(51) Int. Cl.

| | | |
|---|---|---|
| C02F 11/04 | (2006.01) | |
| C12M 1/107 | (2006.01) | |
| C12M 1/34 | (2006.01) | |
| C12M 1/00 | (2006.01) | |
| C12M 1/02 | (2006.01) | |
| C05F 17/40 | (2020.01) | |
| C05F 17/50 | (2020.01) | |

(52) U.S. Cl.
CPC ............ *C12M 21/04* (2013.01); *C12M 29/24* (2013.01); *C12M 41/12* (2013.01); *C12M 41/18* (2013.01); *Y02E 50/343* (2013.01); *Y02P 20/129* (2015.11); *Y02P 20/133* (2015.11); *Y02P 20/145* (2015.11); *Y02W 10/23* (2015.05); *Y02W 30/43* (2015.05); *Y02W 30/47* (2015.05)

(58) Field of Classification Search
USPC ................................. 435/290.1, 290.2, 300.1
See application file for complete search history.

(56) References Cited

U.S. PATENT DOCUMENTS

| | | |
|---|---|---|
| 4,057,401 A | 11/1977 | Boblitz |
| 4,100,023 A | 7/1978 | McDonald |
| 4,133,273 A | 1/1979 | Glennon |
| 4,209,303 A | 6/1980 | Ricks |
| 4,213,857 A | 7/1980 | Ishida et al. |
| 4,230,580 A | 10/1980 | Dodson |
| 4,246,099 A | 1/1981 | Gould et al. |
| 4,252,901 A | 2/1981 | Fischer et al. |
| 4,274,838 A | 6/1981 | Dale et al. |
| 4,289,625 A | 9/1981 | Tarman et al. |
| 4,323,367 A | 4/1982 | Ghosh |
| 4,342,836 A | 8/1982 | Harvey |
| 4,354,936 A | 10/1982 | Ishida et al. |
| 4,436,817 A | 3/1984 | Nemetz |
| 4,442,006 A | 4/1984 | Ishida et al. |
| 4,521,310 A | 6/1985 | Casey |
| 4,522,721 A | 6/1985 | Ishida et al. |
| 4,551,243 A | 11/1985 | Martin |
| 4,568,457 A | 2/1986 | Sullivan |
| 4,735,724 A | 4/1988 | Chynoweth et al. |
| 4,750,454 A | 6/1988 | Santina et al. |
| 4,780,415 A | 10/1988 | Ducellier et al. |
| 4,798,802 A | 1/1989 | Ryan |
| 4,857,458 A | 8/1989 | Nobilet et al. |
| 5,091,315 A | 2/1992 | McCarty et al. |
| 5,207,911 A | 5/1993 | Pellegrin et al. |
| 5,409,610 A | 4/1995 | Clark |
| 5,451,319 A * | 9/1995 | Kobayashi ................ C02F 3/28 210/603 |
| 5,453,376 A | 9/1995 | Ek |
| 5,496,730 A | 3/1996 | Teramachi |
| 5,527,464 A | 6/1996 | Bartha et al. |
| 5,587,320 A | 12/1996 | Shindo et al. |
| 5,593,590 A | 1/1997 | Steyskal |
| 5,611,926 A * | 3/1997 | Nishida ................ B01D 17/0214 210/242.3 |
| 5,637,219 A | 6/1997 | Robinson et al. |
| 5,672,506 A | 9/1997 | Aoyagi et al. |
| 5,710,042 A | 1/1998 | Shindo et al. |
| 5,772,887 A | 6/1998 | Noah et al. |
| 6,048,458 A | 4/2000 | Vogt et al. |
| 6,087,155 A | 7/2000 | York et al. |
| 6,103,191 A | 8/2000 | Luker |
| 6,139,744 A | 10/2000 | Spears et al. |
| 6,168,642 B1 | 1/2001 | Valkanas et al. |
| 6,254,775 B1 | 7/2001 | McElvaney |
| 6,299,744 B1 | 10/2001 | Narayanan et al. |
| 6,342,378 B1 | 1/2002 | Zhang et al. |
| 6,410,283 B1 | 6/2002 | Rehmat et al. |
| 6,451,589 B1 | 9/2002 | Dvorak |
| 6,521,129 B1 | 2/2003 | Stamper et al. |
| 6,551,510 B1 | 4/2003 | Bakke et al. |
| 6,613,562 B2 | 9/2003 | Dvorak |
| 6,663,777 B2 | 12/2003 | Schimel |
| 6,673,243 B2 | 1/2004 | Srinivasan et al. |
| 6,824,682 B2 | 11/2004 | Branson |
| 6,855,253 B2 | 2/2005 | Baumgartner et al. |
| 6,929,744 B2 | 8/2005 | Le |
| 6,982,035 B1 | 1/2006 | O'Keefe |
| 6,984,305 B2 | 1/2006 | McAlister |
| 7,078,229 B2 | 7/2006 | Dvorak |
| 7,179,642 B2 | 2/2007 | Dvorak |
| 8,202,721 B2 | 6/2012 | Dvorak |
| 8,394,271 B2 | 3/2013 | Dvorak |
| 8,414,808 B2 | 4/2013 | Dvorak et al. |
| 8,470,177 B2 | 6/2013 | Dvorak |
| 2004/0164019 A1 | 8/2004 | Fassbender |
| 2006/0096163 A1 | 5/2006 | Dickinson et al. |
| 2007/0193948 A1 | 8/2007 | Livingston et al. |
| 2008/0251439 A1 | 10/2008 | Pollock |
| 2008/0277336 A1 * | 11/2008 | Dvorak .................. A01C 3/023 210/603 |
| 2009/0107913 A1 | 4/2009 | Johnson |
| 2010/0201026 A1 | 8/2010 | Dvorak |

FOREIGN PATENT DOCUMENTS

| | | | |
|---|---|---|---|
| EP | 0213691 A2 | 11/1987 | |
| EP | 1081100 | 7/2001 | |
| EP | 1150083 A1 * | 10/2001 | ............ C02F 11/12 |
| GB | 1561573 | 2/1980 | |
| JP | 10225674 | 8/1998 | |
| JP | 11104601 | 4/1999 | |
| WO | 2008066508 A1 | 6/2008 | |
| WO | 2008066546 A1 | 6/2008 | |
| WO | WO 2008066546 A1 * | 6/2008 | ............ C02F 3/286 |
| WO | 2008140986 A1 | 11/2008 | |
| WO | 2011066393 | 6/2011 | |

OTHER PUBLICATIONS

Kraus Oliver, "English language translation of EP 1150083A1", translated on Jun. 9, 2016.*
Unicorn Distributed Energy, The Next Generation of Power brochure, 2 pgs., printed 1999.
Non-Final Office Action dated Jul. 1, 2010 for U.S. Appl. No. 11/563,574, filed Nov. 27, 2006.
A Manual for Developing Biogas Systems at Commercial Farms in the United States; AgSTAR Handbook; Jul. 1997, EPA.
International Preliminary Report on Patentability for PCT App. No. PCT/US2010/058012 dated May 30, 2012.
Wilke, A.; Anaerobic Treatment of Agricultural Wastes, "Dairy Waste Fixed Film Digester Design Example," presentation, no date, 10 pgs.
Wilkie, A.; Anaerobic Digestion: Holistic Bioprocessing of Animal Manures; no date, 15 pgs, Soil and Water Science Depart., University of Florida, Gainsville, FL USA.
Williams, C.; The Feasibility of Thermophilic Anaerobic Digestion for Treating Animal Wastes; no date, 10 pgs, Animal & Poultry Waste Management Center; North Carolina State University, Raleigh, NC USA.
Williams, C. et al; Baseball Stadium Hits Home Run for Recycling and Composting, magazine, Feb. 2005, p. 56, BioCycle.
Witherspoon, J. et al; Public Enemy No. 1 for Biosolids, magazine, May 2004, pp. 31-35, WE&T.
Wright, P.; Anaerobic Treatment of Agricultural Wastes, "Design & Operational Considerations (Part 1)," presentation, no date, 17 pgs.
Wright, P.; Anaerobic Treatment of Agricultural Wastes, "Design & Operational Considerations (Part 2)," presentation, no date, 24 pgs.
Wright, P.; An Economic Comparison of Two Anaerobic Digestion Systems on Dairy Farms, presentation, Jul. 27-30, 2003, 7 pgs, 2003 ASAE Annual International Meeting, Las Vegas, Nevada, USA.

(56) References Cited

OTHER PUBLICATIONS

Wright, P.; Anaerobic Treatment of Agricultural Wastes, "Dairy Plug Flow Digester Design Example," presentation, no date, 18 pgs.
Yen, H et al; Anaerobic co-digestion of algal sludge and waste paper to produce methane, available online Jan. 4, 2006, 1 pg, from website: ScienceDirect—Bioresource Technology.
PCT International Search Report dated Mar. 12, 2007 for PCT/US06/45414 filed Nov. 27, 2006.
PCT International Preliminary Report on Patentability Written Opinion of the International Search Authority dated Jun. 3, 2009 for PCT/US06/45414 filed on Nov. 27, 2006.
PCT International Search Report dated Oct. 1, 2007 for PCT/US2006/61252 filed on Nov. 27, 2006.
PCT International Preliminary Report on Patentability Written Opinion of the International Searching Authority dated Jun. 3, 2009 for PCT/US2006/61252 filed on Nov. 27, 2006.
PCT International Search Report dated Oct. 10, 2008 for PCT/US2008/062624 filed on Oct. 10, 2008.
PCT International Preliminary Report on Patentability Written Opinion of the International Searching Authority dated Nov. 10, 2009 for PCT/US2008/062624 filed on May 5, 2008.
GHD's Steve Dvorak: Farming Biopower from Manure, quarterly magazine, Winter 2004, pp. 6-7, The Renewable Quarterly.
Goodrich, P.; Anaerobic Digester Systems for Mid-Sized Dairy Farms; report, no date, 45 pgs, AgSTAR Fund for Rural America, The Minnesota Project; Minnesota.
Greer, D.; Creating Cellulosic Ethanol, "Spinning Straw Into Fuel," magazine, Apr. 2005, pp. 61-67, Biocycle.
Han, Y. et al; Temperature-phased anaerobic digestion of wastewater sludges; 1997, vol. 36, No. 6-7, pp. 367-374, Wat. Sci. Tech., Great Britain.
Hanaki, K. et al; Mechanism of inhibition caused by long-chain fatty acids in anaerobic digestion process; 1981, vol. XXIII, pp. 1591-1610, Biotechnology and Bioengineering.
Hansen, C.; Anaerobic Treatment of Agricultural Wastes, "Swine Waste Mixed Flow Digester Design Example," presentation, no date, 17 pgs.
Hansen, R.; Methane Generation From Livestock Wastes, fact sheets, printed Jul. 10, 2003, 6 pgs, Colorado State Univ. Cooperative Extension, from website: http://www.ext.colostate.edu/pubs/farmmgt/ 05002.html.
Hanusa, D.; Anaerobic Treatment of Agricultural Wastes, "Biogas Handling & Use," presentation, no date, 17 pgs.
Harlow, S.; A dairy goes on the grid, magazine, May 2005, 3 pgs, Environment, reprinted w/permission from Northeast DairyBusiness.
Harrison, J. et al; Evaluation of the pathogen reduction from plug flow and continuous feed anaerobic digesters, article, no date, 6 pgs.
Harrison, J.; Anaerobic digesters & pathogens?, publication, no date, 1 pg, vol. 14, No. 1, WSE Dairy News.
Hoenig, S.; Anaerobic Digestion "A new way to handle manure," magazine, Mar. 1998, 2 pgs, Resource.
Hoff, M.; Final Report, Matt Hoff—Methane Digestion and Composting Feasibility Study, report, Jan. 2006, 70 pgs, EA Engineering, Science and Technology, Inc.
Holmberg, W. et al; Integrated farm energy systems: Building a better biorefinery, printed Jan. 24, 2001, 10 pgs, from website: www.biogasworks.com/reports.
Hopps, D. et al; Yakima Valley Dairy Manure Conversion Project, "USDA Value Added Producer Grant Program," feasibility study, Jan. 2006, 46 pgs.
How the Biocoil Works—The Biocoil Operations Manual, printed Apr. 7, 2005, 2 pgs, from website: http://www.cscadehs.csd.k12.id.us/advbio/95-96/biomanual.html.
Humic Acid/Substances, printed Dec. 12, 2006, 3 pgs, Goodrich World, from website: http://www.goodrichworld.com/humic-acid-substances.html.
Humifulvate® A Natural Active Ingredient, article, printed Dec. 26, 2006, 7 pgs, from website: http://www.enerex.ca/articles/some_humifulvate_science.htm.

Hwu, C. et al; Biosorption of longchain fatty acids in UASB treatment process; publication, 1998, vol. 32, No. 5, pp. 1571-1579, Wat. Res., Great Britain.
Idaho Dairy Waste Conversion to Electricity—A Pilot Project Feasibility Study, Final Report, Oct. 2004, 87 pgs.
Introduction to Anaerobic Digestion, printed Jan. 17, 2001, 2 pgs, from website: http://biogasworks.com/Index/AD%20Intro.htm.
Ito, T. et al; Hydrogen and Ethanol Production from Glycerol-Containing Wastes Discharged after Biodiesel Manufacturing Process, publication, 2005, pp. 260-265, vol. 100, No. 3, Journal of Bioscience and Bioengineering, The Society for Biotechnology, Japan.
Jet Tech "Class A" Auto-thermal thermophilic aerobic digestion (ATAD); 1986, 2 pgs, Jet Tech, Inc. from website.
Jewell, W.; Anaerobic sewage treatment; publication, 1987, pp. 14-21, vol. 21, No. 1, Environ. Sci. Technol.
Johnson, R.; Manure Digester Generates Income, Savings, newspaper, Apr. 3, 2003, 3, pgs, AGRI-VIEW.
Journey, W. et al; Anaerobic Enhanced Treatment of Wastewater and Options for Further Treatment; report, Nov. 1996, 95 pgs, ACDI/VOCA; Washington, DC, USA.
Kepp, U. et al; Enhanced stabilization of sewage sludge through thermal hydrolysis—three years of experience with full scale plant; publication, 2000, vol. 42, No. 9, pp. 89-96, Water Science & Technology.
Keusch, P.; Hard Water Kills Soap, "Objective: The Influence of Hard Water on the Washing Process," Dec. 21, 2006, 2 pgs, from website: http://www.uni-regensburg.de/Fakultaeten/nat_Fak_IV/Organische_Chemie/Didaktik/Keusch/D-hard_water . . . .
Koeslch, R. et al.; Anaerobic Digesters for Dairy Farms, Extension Bulletin 45, no date, 74 pgs, Department of Agricultural and Biological Engineering; New York State College of Agriculture and Life Sciences, Ithaca, NY, USA.
Komiyama, M. et al; Biogas as a reproducible energy source: Its steam reforming for electricity generation and for farm machine fuel, publication, 2006, pp. 234-237, International Congress Series 1293, Elsevier B.V.
Koster, I. et al; Inhibition of Methanogenesis from Acetate in Granular Sludge by Long-Chain Fatty Acids; publication, Feb. 1987, pp. 403-409, Vo.. 53, No. 2, Applied and Environmental Microbiology.
Kramer, J.; Agricultural Biogas Casebook—2004 Update, report, Sep. 2004, 69 pgs.
Krishnan, V. et al; Effect of coagulation on palm oil mill effluent and subsequent treatment of coagulated sludge by anaerobic digestion, publication, (2006), 81:1652-1660, Journal of Chemical Technology and Biotechnology.
Lasonde, W., Drying, burning and creating energy with manure, presentation to Dairy Business Associates , no date, 5 pgs.
Lemley, B., Anything into Oil, May 2003, 9 pgs, Discover vol. 24, No. 5, publication from website: http://www.discovery.com/may_2003/featoil.html.
Leonardite Extract, printed Dec. 12, 2006, 2 pgs, from website: http://www.Igagro.com/HumicAcid.htm.
Lipase—Wikipedia, printed Dec. 12, 2006, 2 pgs, from website: http://en.wkkipedia.org/wiki/Lipase.
Livestock Manure Management; Summary; Sep. 1999, pp. 1-16, Chapter 5, US EPA.
Lorimor, J.; Anaerobic Digestion for 5000 Head Sow Facility, presentation, no date, 14 pgs.
Lorimor, J.; Anaerobic Treatment of Agricultural Wastes, "Dairy Waste Plug Flow Digester Design Examples," presentation, no date, 13 pgs.
Lorimor, J.; Anaerobic Treatment of Agricultural Wastes, "Swine Waste Digester Design Example," presentation, no date, 9 pgs.
Lusk, P., Anaerobic Treatment of Agricultural Wastes, "Economic Considerations for Anaerobic Digestion," presentation, no date, 27 pgs, Resource Development Associates, Pierre, SD, USA.
Lusk, P.; Anaerobic Digestion and Opportunities for International Technology Transfer; magazine, no date, 4 pages, CADDET; United Kingdom.

(56) References Cited

OTHER PUBLICATIONS

Lusk, P.; Methane recovery from animal manures: The current opportunities casebook; Sep. 19, 1998, pp. 21-26, Chapter 2, National Energy Renewable Laboratory.
Mackie, R. et al; Anaerobic digestion of cattle waste at mesophilic and thermophilic temperatures, publication, 1995, 43: 346-350, Appl. Microbiol Biotechnol.
Manure Processing Technologies, printed Aug. 5, 2005, 10 pgs, from website: http://res2.agr.gc.ca/initiatives/manurenet/en/man_tech.html, ManureNet, Agriculture and Agri-Food Canada.
Martin, J.; An Evaluation of a Mesophilic, Modified Plug Flow Anaerobic Digester for Dairy Cattle Manure, report, Jul. 20, 2005, 38 pgs, EPA Contract No. GS 10F-0036K, Work Assignment/Task Order No. 9.
Martin, J; A Comparison of Dairy Cattle Manure Management with and without Anaerobic Digestion and Biogas Utilization, report, Mar. 17, 2003, 58 pgs, EPA Contract #68-W7-0068, Task Order 400.
Massart, N. et al; When It Bubbles Over Excessive foam is a symptom of unstable digester conditions, publication, 2006, vol. 18, No. 10 pp. 50-55, Water Environment Federation, USA.
Mattocks, R.; Is a manure digestion system the answer for you?, magazine, Jul./Aug. 2004, pp. 18-23, Manure Manager.
A Centralised Thermophilic Biogas Plant in Denmark; Tech Brochure #43; 1996; 4 pgs, Caddet; United Kingdom.
A Long History of Digesters that Work, newsletter, Sep. 2004, RCM Digesters, Inc., Berkeley, CA, USA.
Agricultural Waste Characteristics; Agricultural Waste Management Field Handbook, 1992, Chapter 4, pp. 1-12; and Anaerobic Digester Technology Application in Animal Agriculture, Jul. 1996, Chapter 10, pp. 72-77 (17 pgs).
Allan, D. et al; Fertilizer Value and Weed Seed Destruction Potential of Digested Manure, presentation, Jun. 2-4, 2003, 12 pgs.
Alleman, J.; Thermophilic Aerobic Processing of Animal Waste Streams, presentation, Nov. 14-16, 1999, 2 pgs, WEF Animal Residuals Conference.
Alternative Technologies/Uses for Manure; draft, no date, pp. 1-35, EPA.
Amon, B. et al; Greenhouse gas and ammonia emission abatement by slurry treatment, publication, International Congress Series 1293 (2006) pp. 295-298 Elsevier, B.V.
Amon, T. et al; Biogas production from maize and dairy cattle manure—Influence of biomass composition on the methane yield, abstract, available online Jun. 27, 2006, 2 pgs, from website ScienceDirect.
Anaerobic Digester—Ambient Temperature, Code 365, Sep. 2003, NRCS, NHCP.
Anaerobic Digester at Freund Dairy in East Canaan, CT: A Case study, Oct. 21, 2003, 12 pgs University of Connecticut Cooperative Extension System (article contains references from 1997).
Anaerobic Digesters; printed May 31, 2007, 2 pgs, Alliant Energy, from website: http://www.alliant energy.com/docs/groups/public/documents/pub/p014727.hcsp?print=true.
Anaerobic Digestion of Farm Waste in the UK; Technical Brochure No. 60, 1997, 4 pgs, CADDET; United Kingdom.
Anaerobic digestion of Piggery Wastes in Victoria, Australia; Technical Brochure No. 4, 1994, 4 pgs, CADDET.
Anaerobic digestion, printed Nov. 8, 2006, 4 pgs, from website: http://www.btgworld.com/technologies/anaerobic-digestion.html.
Anaerobic Systems in Washington State, "Digesters Bring Power and Income to West Coast Dairy Farms," magazine, Nov. 2004, pp. 54-55, Biocycle.
Anaerobic Treatment of Agricultural Wastes, presentation contents sheet, Nov. 3-5, 2003, 1 pg, NRCS, Nashville, Tennessee, USA.
Angelidaki, I. et al; Thermophilic anaerobic digestion of livestock waste: the effect of ammonia, publication, 1993, 38:560-564, Appl. Microbiol Biotechnology, Denmark.
Appendix V: Supporting Material for the Analysis of Livestock Manure Management; Sep. 1999, pp. V1-V7 and p. 5-17, U.S. EPA.

Balsam, J.; Anaerobic Digestion of Animal Wastes: Factors to Consider, electronic newsletter, Oct. 2002, pp. 1-12, ATTRA, operated by NCAT.
Biomass Gasifier System, printed Dec. 12, 2006, 4 pgs, Goodrich World, from website: http://www.goodrichworld.com/Biomass-gasifier-system.html.
Blume, E.; Manure Produces Power, magazine, Jul./Aug. 2005, 2 pgs, Engineering Professional.
Boersma, L. et al.; Methods for the Recovery of Nutrients and Energy from Swine Manure, 1981, pp. 3-14, Neth. J. Agric. Science 29.
Bogovich, W. et al; Long Term Operation and Maintenance of a Digester at the Brendle Farms Poultry Operation, presentation, Aug. 1-4, 2004, pp. 1-8, Ontario, Canada, 2004 ASAE/CSAE Annual International Meeting.
Burns, R. et al; Laboratory and In-Situ Reductions of Soluble Phosphorus in Liquid Swine Waste Slurries, printed Apr. 17, 2003, 3 pgs, UT Animal Waste Management, from website: http://wastemgmt.ag.utk.edu/struvite_2.htm.
Burns, R. et al; Phosphorus Recovery from Animal Manures using Optimized Struvite Precipitation, published in Proceedings of Coagulants and Flocculants: Global Market and Technical Opportunities for Water Treatment Chemicals May 22-24, 2002, pp. 1-7, Chicago, IL.
Burns, R.; Anaerobic Treatment of Agricultural Wastes, "Anaerobic Treatment System Configurations," presentation, no date, 16 pgs, University of Tennessee Institute of Agriculture.
Cheng, J et al; Final Report to Dr. C. Mike Williams, Director, NCSU Animal and Poultry Waste Management Center, report, May 20, 2004, 30 pgs.
Cicek, N.; A review of membrane bioreactors and their potential application in the treatment of agricultural wastewater, publication, 2003, vol. 45, pp. 6.37-6.49, Canadian Biosystems Engineering, Manitoba, Canada.
Cleveland, A.; Final report on the use of a bioremediation system on a sewage lagoon at a Dept. of Defense Facility, Nov. 2000, 4 pgs.
Control of Pathogens and Vector Attraction in Sewage Sludge, Oct. 1999, 6 pgs, EPA/625/R-92/013.
Crooks, A; Protecting Forests and Supporting Renewable Energy, magazine, Apr. 2005, vol. 46, No., p. 68 4. pgs. printed from website http://www.jgpress.com/archives/_free/000411.html,BioCycle.
Deluna, J.; Understanding the Hazards of Flame Retardants—Polybrominated diphenyl ethers are becoming more prevalent with unknown long-term effects on humans, magazine, 2003, vol. 15, No. 8, p. 74, Water Environment and Technology (WE&T).
Demirer, G; Effect of retention time and organic loading rate on anaerobic acidification and biogasification of dairy manure, abstract, research article accepted: Jul. 8, 2004, 1 pg, from website: Wiley Interscience: Journal: Abstract.
Digester biochemistry, no date, 1 pg, from website: bungah@rpi.edu.
Digestive Enzyme Facts, printed Dec. 12, 2006, 3 pgs, Beta Force; from website: http://www.beta-glucan-info.com/digestive_enyme_facts.htm.
Dvorak, M.; Improving Herd Health, "Digester Provides Power and Cow Comfort," magazine, Aug. 2005, p. 47, Biocycle.
Dvorak, S.; Anaerobic Treatment of Agricultural Wastes, "Dairy Waste Digester Design Example," presentation, no date, 10 pgs.
Dvorak, S.; Progress in Anaerobic Digesters, "New Markets for Recycled Bedding From Digesters," magazine, Oct. 2004, p. 44, Biocycle.
Emission and reduction of greenhouse gases from agriculture and food manufacturing, report, Dec. 1999, 41 pgs., USDOE.
EPA may target carbon dioxide; newspaper, Feb. 28, 2001, 1 pg, Milwaukee Journal Sentinel, Milwaukee, WI.
Erwin, M.; Iowa Swine Producers Views on CSTR Digester, power point presentation, no date, 5 pgs.
Executive Summary Highlights High Solids Anaerobic Digestion Demonstration/Validation, highlights from report, Dec. 10, 2003, 4 pgs, Orbit LLC.
Farm-Based Anaerobic Digestion Practices in the U.S.; printed Jan. 17, 2001, 6 pgs, from website: biogasworks.com.

(56) References Cited

OTHER PUBLICATIONS

Fedler, C.; Increasing Technical Support, "Recycling Water Saves Future Drinking Supplies," magazine, Feb. 2005, pp. 50-55, Biocycle.
Fee, R.; Common sense could help solve our growing phosphorus problem; magazine, Feb. 2000, p. 31, Successful Farming.
Ford, J., Steve Dvorak, "Dairy Waste Digester Design Example"; Anaerobic Treatment of Animal Wastes Course Agenda, presentation, Nov. 3-5, 2003, 6 pgs, Nashville, Tennessee, USA.
Foster, R.; An Integrated Anaerobic Digester, Power Generation, Composting System in Operation for Twenty-One Years, presentation, no date, 8 pgs.
Foster, R.; Anaerobic Treatment of Agricultural Wastes, "Dairy Producer/Digester Experience," presentation, no date, 16 pgs.
Fronek, S. et al; Changes, "A Plant modifies its conventional mesophilic digesters to a TPAD system for better quality biosolids," magazine, May 2004, pp. 27-30, WE&T.
Methane (Biogas) from anaerobic digesters; printed Feb. 27, 2001, 5 pgs, Consumer Energy Information: EREC Reference Briefs, Energy Efficiency and Renewable Energy Clearinghouse (EREC), Merrifield, VA; from website: doe.erec@nciinc.com.
Miranda, L. et al; A full-Scale UASB Reactor for Treatment of Pig and Cattle Slaughterhouse Wastewater with a High Oil and Grease Content, publication, Oct.-Dec. 2005, vol. 22, No. 04, pp. 601-610, Brazilian Journal of Chemical Engineering, Brazil.
Moen, G.; Anaerobic Digester Foaming: Causes and Solutions, publication, Aug. 2003, pp. 70-73, WE&T.
Moser, M. et al; Benefits, Costs and Operating Experience at Seven New Agricultural Anaerobic Digesters; printed Sep. 5, 2000, 10 pgs, EPA, The AgSTAR Program; from website: www.epa.gov/outreach/atstar/library.
Moser, M.; Anaerobic Digesters Control Odors, Reduce Pathogens, Improve Nutrient Manageability, Can be Cost Competitive with Lagoons, and Provide Energy Tool, printed Jun. 17, 2005, 5 pgs, from website: http://www.epa.gov/agstar/resources/man_man.html, US EPA—AgSTAR—Documents, Tools and Resources.
Mshandete, A. et al; Effect of particle size on biogas yield from sisal fiber waste, abstract, available online Dec. 9, 2005, 1 pg, from website: ScienceDirect—Renewable Energy.
Next Generation of Power (The); article, no date, Unicorn Distributed Energy.
Nielsen, H. et al; Comparison of two-stage thermophilic (68°C/55°C) anaerobic digestion with one-stage thermophilic (55°C) digestion of cattle manure, abstract, printed Nov. 14, 2006, 1 pg, from website: http://www3.interscience.wiley.com/cgi-bin/abstract/107637157/Abstract?CRETRY=1&SRETRY=0, Wiley InterScience.
Nordberg, A. et al; Anaerobic digestion of alfalfa silage with recirculation of process liquid, publication, Bioresource Technology 98 (2007) pp. 104-111, from online at www.sciencedirect.com, Elsevier Ltd.
Nutrient Utilization and Anaerobic Digestion; printed Jan. 17, 2001, 6 pgs, from website: www.biogasworks.com.
Odor, Pathogens, and Anaerobic Digestion; printed Jan. 17, 2001, 4 pgs, from website: http://biogasworks.com.
Oleary, F.; Methane into money, magazine, Apr. 2003, pp. 12-14, Wisconsin Agriculturist.
Oles, J. et al; Full Scale Experience of Two Stage Thermophilic/Mesophilic Sludge Digestion; publication, 1997, pp. 449-456, vol. 36, No. 6-7, Wat. Sci. Tech. 7, Great Britain.
Otto, D. et al; Activation of Mitochondrial Fatty Acid Oxidation by Calcium; publication, Feb. 10, 1978, pp. 789-799, vol. 253, No. 3, The Journal of Biological Chemistry, USA.
Plug-Flow Digester; RDA Summary Model, Oct. 16, 2003, 9 pgs., Biogasworks.com.
Poels, J. et al; Performance, Operation and Benefits of an Anaerobic Digestion System on a Closed Piggery Farm; publication, 1983, pp. 233-249, Agricultural Wastes 8, Applied Science Publishers Ltd., England.
Quaife, T.; Odor control with a paycheck; magazine, Dec. 2000, pp. 28-29, Dairy Heard Management.

Raman, D.; Anaerobic Treatment of Agricultural Wastes, "Anaerobic Treatment of Animal Wastes," presentation, no date, 17 pgs, The University of Tennessee.
Reeves, P. et al; Biological Treatment of Dairy Manure Using Sequencing Batch Reactors: Improving Profitability Through Innovative Design, publication, printed fax from UW Extension on Apr. 14, 1999, pp. 121-124 of Manure Management.
Rico, J. et al; Characterisation of solid and liquid fractions of dairy manure with regard to their component distribution and methane production, abstract, available online Jun. 15, 2006, 1 pg, from website: Science Direct-Bioresource Technology.
Rinzema, A et al; Anaerobic Digestion of Long-Chain Fatty Acids in UASB and Expanded Granular Sludge Bed Reactors; publication, 1993, pp. 527-537, Process Biochemistry 28, Elsevier Science Publishers Ltd., England.
Roberts, R. et al; Two-stage, Thermophilic-Mesophilic Anaerobic Digestion of Sewage Sludge, publication, Mar. 1999, pp. 93-97, vol. 77, Part B, Institution of Chemical Engineers; Trans IChemE., United Kingdom.
Rosentrater, K. et al; Anaerobic Digestion Potential for Ethanol Processing Residues, presentation, Jul. 9-12, 2006, 9 pgs, 2006 ASABE Annual International Meeting, Portland, Oregon, USA.
Roy, F. et al; Influence of Calcium Addition on Growth of Highly Purified Syntropic Cultures Degrading Long-Chain Fatty Acids, publication, Mar. 1985, pp. 702-705, vol. 49, No. 3, Applied and Environmental Microbiology.
Saele, L.; Anaerobic Treatment of Agricultural Wastes, "NRCS Anaerobic Digester Conservation Practice Standards," presentation, no date, 17 pgs, USDA/NRCS.
Saele, L.; Anaerobic Treatment of Agricultural Wastes, "Swine Waste Covered Anaerobic Lagoon Design Example,", presentation, no date, 13 pgs, USDA/NRCS.
Saele, L.; Extended Abstracts of Papers and Posters Presented Manure Management—In Harmony with the Environment and Society; Anaerobic Digester Lagoon with Methane Gas Recovery: First Year Management and Economics; Manure Management, presentation, Feb. 10-12, 1998, pp. 112-124, The Soil and Water Conservation Society, West, North Central Region, Ames, IA.
Saltes, J. et al; Achieve higher effluent quality by recycling settled solids through your rotating biological contactors; magazine, Dec. 2000, pp. 71-74, WE&T.
Saponification, article from Wikipedia, printed Dec. 21, 2006, 2 pgs, from website: http://en.wikipedia.org/wiki/Saponificaiton.
Shaw, R.; Don't forget methane, climate experts say; Nov. 10, 1999, 2 pgs, Environmental News Network, from website: http://biogasworks.com/ News.
Shelef, G.; The combination of Algal and anaerobic waste treatment in a bioregenerative farm system, "Bioconversion of organic residues for rural communities," article, printed Apr. 7, 2005, 8 pgs, from website: http://www.unu.edu/unupress/unupbooks/80434e/80434EOn.htm.
Sievers, D.M. et al; Anaerobic Processes for Stabilization and Gas Production; publication, Nov. 1981, 10 pgs, Research Results in Manure Digestion, Runoff, Refeeding, Odors, University of Missouri-Columbia.
Sludge Stabilization (Reduction); handbook, no date, pp. 1-21, Chapter 5, EPA-WWT Handbook.
Sludge Stabilization; handbook, no date, pp. 1-16, Chapter 11; EPA-VVWT Handbook.
Soap and Saponification—Preparation & Chemical Structure, printed Dec. 21, 2006, 2 pgs, About Chemistry; from website: http://chemistry.about.com/library/ weekly/blsapon.htm.
Solids Separation/Nitrification-Denitrification/Soluble Phosphorus Removal/Solids Processing System (Super Soil Systems USA), article, printed Feb. 22, 2006, 4 pgs, from website: Waste Management Programs, College of Agriculture & Life Sciences, NC State University.
Statement of Qualifications; Jul. 14, 2000, 7 pgs, Taylor & Thomas Environmental, Inc., Dunedia, FL USA.

(56) References Cited

OTHER PUBLICATIONS

Structural & Architectural Precast; printed Oct. 16, 2006, Spancrete, 1 pg. from website: http://www.spancrete.com/os_hollowcore.html.
Study Finds Use of Bioenergy Would Help Reduce Greenhouse Gases, article, printed Jan. 21, 2000, 1 pg, EarthVision Reports, from website: http://earthvision.net/ColdFusion/News_Page1.cfm?NewsID=9225.
Swine-Covered Anaerobic Lagoon-Design Case Study, Barham Farm, report, 1994-1996, 9 pgs, AgSTAR Fund.
Tompkins, D.; Organic Waste treatment using novel composting technologies, summary report, Jul. 2006, 11 pgs, Science Research and Innovation Centre, The University of Plymouth.
Turnquist, A. et al; Manure Management on Wisconsin Farms, PATS Research Report No. 15, Jan. 2006, 23 pgs, University of Wisconsin, Madison, WI USA.
Umetsu, K. et al; Anaerobic co-digestion of dairy manure and sugar beets, abstract, available online Jul. 8, 2006, 2 pgs, from website: ScienceDirect—International Congress Series.
Upgrading Dairy Biogas to Biomethane and Other Fuels, report , no date, Chapter 3 pp. 47-70, Biomethane from Dairy Waste: A Sourcebook for the Production and Use of Renewable Natural Gas in California.
Using Algae to Recycle Flue Gas into Biofuels, blog, Jun. 1, 2006, 3 pgs, from website: BioConversion Blog.
Varel, V. et al; Thermophilic Methane Production from Cattle Waste; publication, Feb. 1977, pp. 298-307, Applied and Environmental Microbiology, Illinois USA.
Vovakes, C.; Stepping on the gas: Dairy turns 'waste' into fuel, published Feb. 17, 2001 2 pgs, from website: sacbee.com archive: Energy crisis.
Walker, L.P. et al.; The Design and Analysis of an Energy Integrated Dairy System; publication, 1984, pp. 229-240, Transactions of the ASAE—1984, American Society of Agricultural, Engineers.
Where: A—Panel size (ft2), power point presentation, no date, 6 pgs.
Why the MBR device is New and Innovative; no date, 4 pgs, Munitech, Inc.; San Antonio, TX USA.

\* cited by examiner

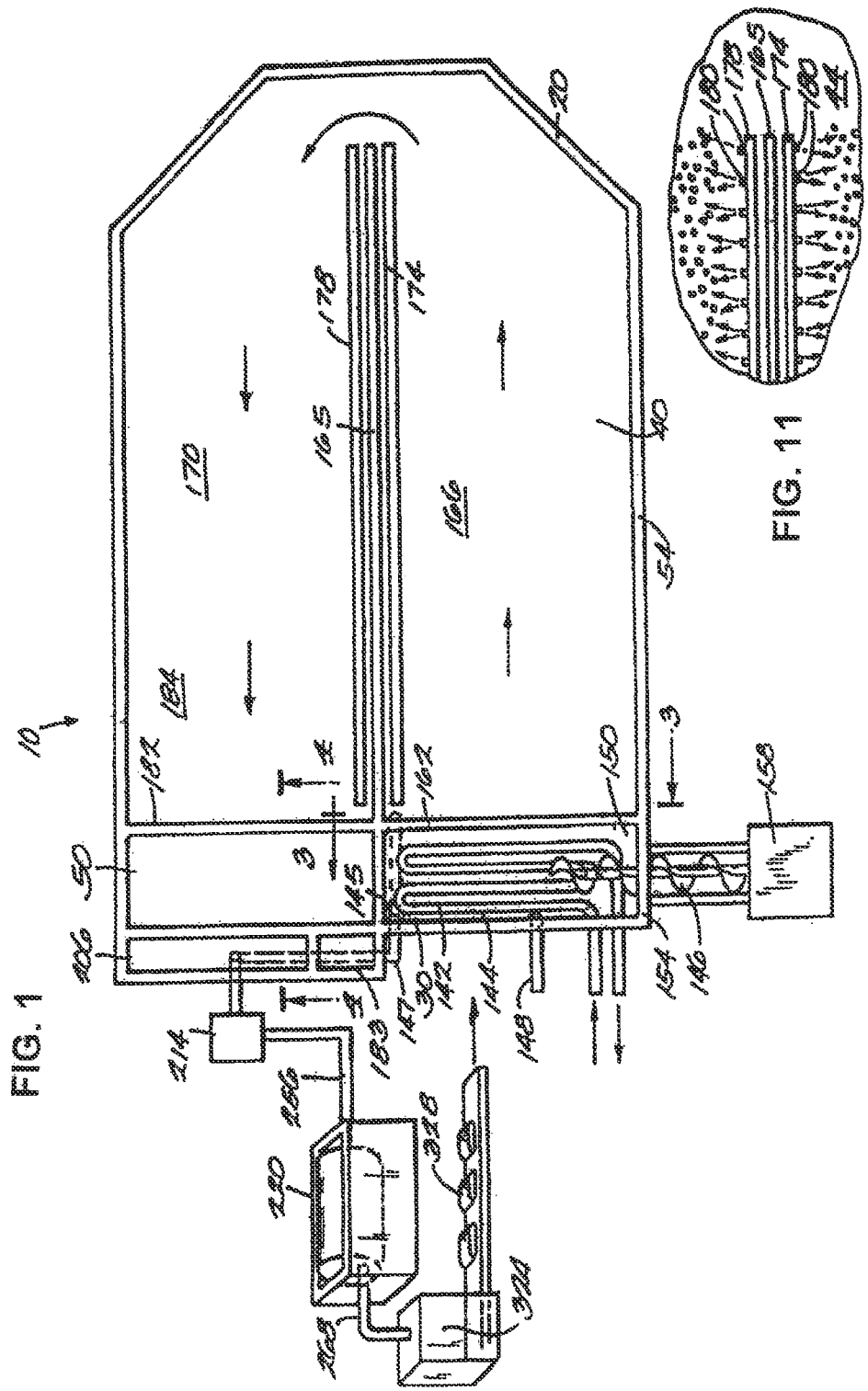

US 10,717,684 B2

BIOSOLIDS DIGESTER AND PROCESS FOR BIOSOLIDS PRODUCTION

CROSS-REFERENCE TO RELATED APPLICATION

This application is a divisional patent application of U.S. patent application Ser. No. 13/511,030 filed May 21, 2012, which is a 371 application of international patent application No. PCT/US2010/058012 Nov. 24, 2010, which claims priority U.S. Provisional Patent Application No. 61/264,420 filed Nov. 25, 2009; the above cited applications are incorporated herein by reference in their entireties.

FIELD

The invention relates to waste-processing systems for processing manure, and other waste material. The invention further relates to apparatuses and methods for the production of Class A biosolids. In yet another embodiment, the invention relates to apparatuses and methods for anaerobic digestion of waste material that yield biosolids with fecal coliform densities that are less than 1,000 Most Probable Number (MPN) per gram total solids (dry weight density).

BACKGROUND

More than $2 billion is spent annually treating and managing approximately 5.3 million dry metric tons of biosolids from publicly owned wastewater treatment plants in the United States (WEF/U.S. EPA Biosolids Fact Sheet Project, Biosolids: A Short Explanation and Discussion, 2000). Land application of biosolids, often to food crops, has gained popularity and widespread approval from the scientific and environmental communities and has increased over the years. National biosolids generation rates are estimated to reach 47 dry pounds per American yearly. In 1972, 20 percent of all U.S. biosolids were land applied, while 40 percent went to landfills. By 1995, 36 percent of all yearly biosolids were land applied, while 38 percent went to landfills. The remainder of the material was incinerated or surface disposed. Disposing of biosolids by shipment to landfills is considered a beneficial use only when such disposal includes methane gas recovery for fuel. Methane operations are relatively rare, however, which establishes land application for soil conditioning and fertilizer as the primary beneficial use of biosolids.

The basic aim of waste material treatment processes is to economically and efficiently reduce and stabilize waste sludge solids. In addition, the sludge treatment system should also produce an end product that is fully suitable for final disposal without further physical or chemical treatment. In conventional practice, final sludge disposal is commonly carried out by incineration, land filling or land spreading. In many instances, land disposal is employed and is particularly attractive due to minimal long-term environmental effects and is highly advantageous in reconditioning of the soil. However, the use of land spreading as a final sludge disposal method may require a well stabilized and pasteurized end product; the concentration of pathogenic organisms in the sludge must be sufficiently low to avoid becoming a health hazard. Also, the sludge should be adequately stabilized to prevent further degradation in the environment and the attraction of vectors.

Traditionally, three distinct processes have been widely utilized for treating wastewater sludges: oxidation ponds, anaerobic digestion and aerobic digestion. Oxidation ponds are generally employed in the form of comparatively shallow excavated earthen basins that extend over a large area of land and retain wastewater prior to its final disposal. Such ponds permit the biological oxidation of organic material by natural or artificially accelerated transfer of oxygen to the pond water from the ambient air. The use of oxidation ponds, however, has limited utility, since their operation requires sizable land areas. Moreover, no significant reduction of the level of pathogens in the sludge and only limited reduction in the quantity of the waste sludge is accomplished by this elementary treatment and disposal method.

The process of anaerobic digestion has generally been the most extensively used wastewater sludge digestion process for stabilizing concentrated organic solids. In common practice, the combined excess waste sludge is accumulated in large covered digesters where the sludge is mixed and naturally fermented anaerobically for about 30 days. The major reasons for the widespread commercial use of anaerobic sludge digestion are that this method can be used to: (1) stabilize large volumes of dilute organic slurries; (2) produce significant biological solids (biomasss) reduction and stabilization; (3) produces a final sludge, wherein water is easily removed, for ultimate disposal; (4) produce methane gas; and (5) produce a pasteurized sludge under the right conditions. Anaerobic digestion is characteristically carried out in large scale tanks that are more or less thoroughly mixed, either by mechanical means or by recirculation of compressed digester gas. Mixing rapidly increases the rate of the sludge stabilization reactions by creating a large zone of active decomposition. In the past, the use of anaerobic digesters has been limited due to high energy demands, which translates into high cost for the end user.

Biosolids also are known to contain pathogens that include viruses, bacteria, and various parasitic organisms. There are generally two classes of biosolids recognized in the United States Environmental Protection Agency's (EPA) regulations: Class B pathogen reduction standards, as set forth in 40 C.F.R. § 503, which require a fecal coliform level of less than two million most-probable-number (MPN) per gram of total solids, and Class A pathogen standards set forth in 40 C.F.R. § 503. EPS's Class A biosolids requirements are satisfied when fecal coliform densities are less than 1,000 MPN per gram total solids; or when Salmonella densities are less than 3 MPN per four grams total solids. Additionally, enteric virus must be less than 1 plaque-forming unit per four grams of total solids, and helminth ova is less than one viable helminth ova per four grams of total solids.

The majority of applications of anaerobic digestion to wastewater sludges have been in the mesophilic temperature range, from 35° C. to 40° C. (95° F. to 104° F.). Anaerobic sludge digestion in the thermophilic temperature range from 45° C. to 65° C. (113° F. to 149° F.) has been practiced to only a limited extent. The limited use of anaerobic digestion at temperatures above the mesophilic range may due to higher energy requirements to obtain the higher thermophilic temperature.

Meeting Class A standards will significantly increase the opportunity for biosolids recycling, however, known processes that achieve Class A pathogen densities in biosolids are generally costly, and in most instances, cost prohibitive. Therefore, a need still exists for methods and processes that can produce Class A biosolids in an efficient and effective manner.

BRIEF SUMMARY

The apparatus and methods disclosed herein provide a waste-processing system capable of processing high-solids waste. The apparatuses and methods discussed herein relate to a waste processing system to produce Class A biosolids.

Methods for optimizing energy requirements associated with biosolid processing and detoxification are disclosed. The methods disclosed comprise coupling the energy demands of Class A biosolid waste material treatment with the energy yield obtained from the conversion of methane byproducts into useable energy.

In one embodiment, disclosed herein is a method of producing Class A biosolids comprising: digesting waste material in an anaerobic digester; passing the digested waste material from the anaerobic digester to a heating pit, and heating the digested waste material in a heating pit using a heating device, wherein the heating device induces the waste material to move in a cork-screw-like fashion; and further wherein the anaerobic digester and heating pit are located within a single closed container.

In another embodiment, disclosed herein is a method for the production of Class A biosolids comprising: digesting waste material in an anaerobic digester comprising a liquid or gas diffuser and using the diffuser to move the waste material in a corkscrew-like flow path through at least a portion of the digester, wherein a first passage and a second passage are separated by a center wall, the digester has outside walls, and the center wall and outside walls are substantially planar and vertical; passing the digested waste material from the anaerobic digester to a heating pit; and heating the digested waste material in a heating pit using a heating device, wherein the heating device includes the waste material to move in a cork-screw-like fashion.

In yet another embodiment, the method comprises using a heating device positioned in at least a portion of one of the first passage and the second passage to heat the waste material to cause thermal mixing of the waste.

In another embodiment, disclosed herein is a method for the production of Class A biosolids comprising: positioning a heating device in a heating pit comprising a liquid diffuser or gas diffuser; moving waste material in a corkscrew-like flow path through at least a portion of the heating pit using said diffuser; and heating said waste material to a temperature from 135° to 180° F.

In another embodiment, the method comprises positioning the diffuser adjacent one of the outside walls, wherein the diffuser provides forces that cause sludge to rise near the outer wall. In still another embodiment, the method comprises using the heating device with heating pipes to enhance convection and facilitate the corkscrew-like flow path.

In another embodiment, disclosed herein is a method for the production of Class A biosolids comprising: placing waste material in a mixing chamber of a digester, wherein said mixing chamber comprises heating coils that can heat at least to 100° F.; digesting the waste material in a methanogenic chamber of the digester; heating the digested waste material in a heating pit, wherein the waste material reaches a temperature from 140° F. to 180° F.; plug-flowing the waste material through the heating pit over a weir wall into an effluent pit; and separating solids and liquid waste material stored in the effluent pit.

In another embodiment, the method further comprises using a heating device to heat the waste material, wherein the heating device induces the waste material to move in a cork-screw-like fashion. In yet another embodiment, the heating device comprises a liquid diffuser or gas diffuser.

In another embodiment, disclosed herein is a method for producing Class A biosolids comprising placing unprocessed waste material in a mixing chamber of a digester; removing solid particulates from the mixing chamber; digesting the waste material for a specified period of time; heating the digested waste material in a heating pit, wherein the waste material reaches a desired temperature; and plug-flowing the waste material to an effluent pit. In another embodiment, the waste material in the effluent pit is pumped into a separator to separate collecting liquid waste in an effluent pit, wherein surplus heat from the liquid waste will be collected and recycled for additional use.

In yet another embodiment, disclosed herein is a method for the production of Class A biosolids comprising: positioning a liquid diffuser or gas diffuser in a heating pit; and using the diffuser to move waste material in a corkscrew-like flow path through at least a portion of the heating pit, wherein the heating pit has outside walls and optionally, a center wall, wherein the optional center wall and outside walls are substantially planar and vertical.

In one embodiment, disclosed herein is a waste processing system comprising: a closed container comprising an anaerobic digester with a first passage and a second passage separated by a center wall, wherein the digester has outside walls, and further wherein the center wall and outside walls are substantially planar and vertical; and a heating pit that is adjacent to the anaerobic digester and shares a wall with the anaerobic digester, wherein the heating pit comprises a first heating device with heating pipes.

In another embodiment, disclosed herein is a waste processing system comprising: a closed container comprising an anaerobic digester with a first passage and a second passage separated by a center wall, wherein the digester has outside walls, and further wherein the center wall and outside walls are substantially planar and vertical; a heating pit that is adjacent to the anaerobic digester and shares a common wall with the anaerobic digester, wherein the heating pit comprises a first heating device to move waste material in a cork-screw-like fashion; and an effluent pit that is adjacent to and shares a common wall with the heating pit, and wherein the effluent pit comprises heating racks to capture excess heat.

In another embodiment, the heating pit is configured to store one day of waste material. In yet another embodiment, the effluent pit is configured to store one day of waste material. In still another embodiment, the heating pit is configured to contain a minimum of one day's storage of waste material, an element that can not be satisfied with totally mixed digesters.

In another embodiment, disclosed herein is a waste processing system comprising: a closed container comprising an anaerobic digester including a mixing chamber, wherein said mixing chamber comprises heating coils that can heat at least to 100° F.; and a methanogenic chamber for digesting the waste material; a heating pit that is adjacent to and shares a common wall with the methanogenic chamber, wherein the heating pit comprises a weir wall for plug flowing the waste material from the methanogenic chamber, and further wherein the waste material is heated to a temperature from 140° F. to 180° F. in the heating pit; and an effluent pit that is adjacent to the heating pit, wherein the effluent pit comprises heating racks for capturing excess heat from the waste material.

In another embodiment, the system comprises a hot water tank to supply heat to the methanogenic chamber. In yet another embodiment, the system comprises an engine, wherein exhaust air from the engine can be supplied to the heating pit for mixing of the waste material.

In another embodiment, heating pipes heat the sludge using, for example, hot water, exhaust, gas, biogas or any combination of the above-recited compounds causing the heated mixed sludge to rise under convective forces in the digester and the heating pit. The convective forces cause the sludge to follow a circular flow path downward along the outer wall, resulting in a combined corkscrew-like flow path for the sludge. The corkscrew effect allows efficient mixing of the sludge through the digester and the heating pit.

In another embodiment, convective forces process the sludge in a corkscrew-like path through the heating pit and into the effluent pit.

In yet another embodiment, the invention relates to a system comprising an anaerobic digester employing a mixed-plug flow design to produce Class A biosolids. In one embodiment, the anaerobic digester comprises a mixing chamber, a digester, a heating pit, and an effluent pit.

The heating pit can be located at any location that allows for the production of Class A biosolids including but not limited to the front or rear of the digester. In one embodiment, the heating pit is located after the digester vessel of the anaerobic digester. The digested material within the heating cell can be heated to any appropriate temperature that produces Class A biosolids including but not limited to 130-135° F., 135-140° F., 140° F., 141° F., 142° F., 143° F., 144° F., 145° F., 146° F., 147° F., 148° F., 149° F., 150° F., 151° F., 152-160° F., 160-170° F., and greater than 170° F.

In another embodiment, disclosed herein are methods for utilizing waste heat in an anaerobic digestion process. The co-gen engines used in the anaerobic digester generate waste heat. This heat may be collected and used to meet the heating demands of the thermophilic phase of the treatment process, and/or drying of the digested sludge. Furthermore, heat and electricity generated in excess of that used in the anaerobic digestion process can be used as a power source to meet other energy requirements. Furthermore, waste heat and electricity from the generation step may be used to dry the Class A biosolids to the appropriate level. These and other additional aspects and advantages are achieved in a unique combination of methods and systems for producing Class A biosolids in an anaerobic digester according to the invention.

The methods and apparatuses disclosed herein advantageously allow for reducing high energy costs associated with Class A biosolid production by utilizing methane byproducts as a renewable energy supply.

An advantage of the methods and apparatuses disclosed herein is the reduction of external energy requirements/costs associated with the production of Class A biosolids.

An advantage of the methods and apparatuses disclosed herein is the conversion of waste heat into utilized energy.

An advantage of the methods and apparatuses disclosed herein is the design of a single closed container capable of generating Class A biosolids.

An advantage of the methods and apparatuses disclosed herein is the use of exhaust air to heat waste material in a heating pit.

An advantage of the methods and apparatuses disclosed herein is the ability to capture excess energy from the waste material using heating racks in an effluent pit.

An advantage of the methods and apparatuses disclosed herein is an energy efficient mechanism to produce Class A biosolids.

An advantage of the methods and apparatuses disclosed herein is the waste material does not need to be filtered prior to heating to a suitable temperature to produce Class A biosolids.

An advantage of the methods and apparatuses disclosed herein is that a pasteurization step is not required.

BRIEF DESCRIPTION OF THE DRAWINGS

FIG. 1 is a schematic view of a waste processing system embodying the invention.

FIG. 11 is an enlarged view of a portion of the waste processing system shown in FIG. 1.

Figures 2, 5:
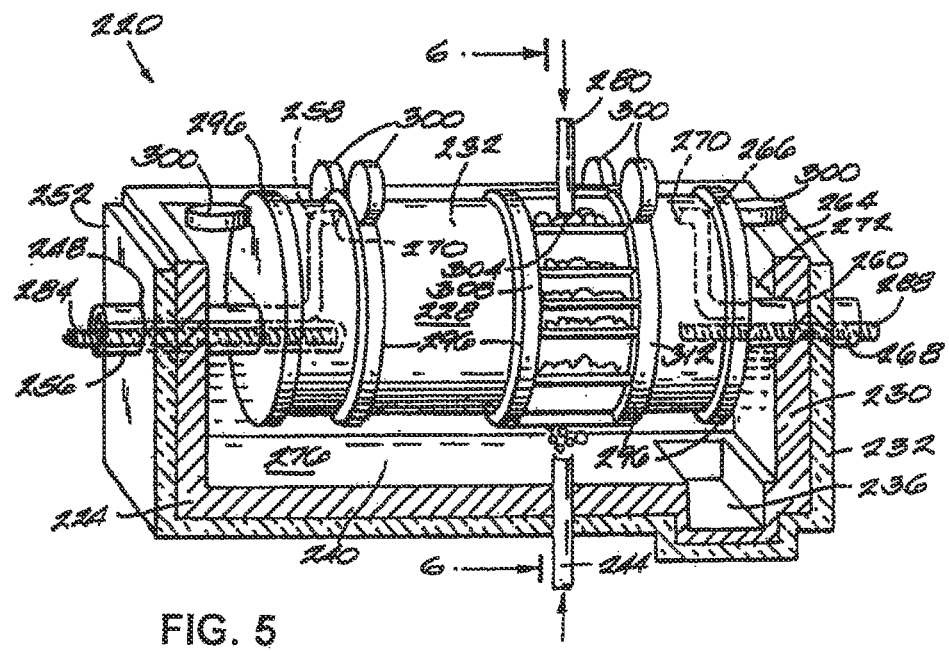
FIG. 2 is a partial cross-section elevational view of the digester of the waste processing system shown in FIG. 1.
FIG. 5 is a perspective view of a composter of the waste processing system shown in FIG. 1.

Before one embodiment is explained in detail, it is to be understood that the methods and the arrangements disclosed herein are not limited in application to the details of construction and the arrangements of the components set forth in the following description or illustrated in the drawings. The methods and apparatuses are capable of other embodiments and of being practiced or being carried out in various ways. Also, it is understood that the phraseology and terminology used herein is for the purpose of description and should not be regarded as limiting. The use of "including" and "comprising" and variations thereof herein is meant to encompass the items listed thereafter and equivalents thereof as well as additional items.

DETAILED DESCRIPTION

Definitions

The numerical ranges in this disclosure are approximate, and thus may include values outside of the range unless otherwise indicated. Numerical ranges include all values from and including the lower and upper values, in increments of one unit, provided that there is a separation of at least two units between any lower value and any higher value. As an example, if a compositional, physical or other property, such as, for example, molecular weight, viscosity, melt index, etc., is from 100 to 1,000, it is intended that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, relative amounts of components in a mixture, and various temperature and other parameter ranges recited in the methods.

The term "Class A biosolid(s)" as used herein refers to material that has met the requirements of 40 C.F.R. § 503.32 as codified in the statutes as of July 2009. In general, EPA Class A pathogen requirements are met in biosolids when fecal coliform densities are less than 1,000 Most Probable Number (MPN) per gram total solids (dry weight density); or when Salmonella densities are less than 3 MPN per four grams total solids at the time the material is used or disposed; at the time the material is prepared for sale or given away in a bag or other container for application to the land; or at the time the material is prepared to meet the requirements of the various alternatives under § 503.32. Enteric virus density must be less than one plaque-forming unit (pfu) per four grams of total solids (dry weight basis) and helminth ova is less than one viable helminth ova per four grams of total solids. Additionally, the EPA provides time and temperature requirements under 40 C.F.R. § 503.32 (a) (3)—Alternative 1, that state the required reduction in pathogen densitites. 40 C.F.R. § 503.32 is herein incorporated by reference as the standard for Class A biosolids.

As used herein, the term "manure" refers to animal wastes including animal dejections, feed remains and hair.

As used herein, the term "heating pit" refers to a container that is used to heat material. The material includes digested waste, partially digested waste, liquid waste, solid waste, and liquid and solid waste.

As used herein, the term "effluent pit" refers to a container that is used to store waste material. The material includes digested waste, partially digested waste, liquid waste, solid waste, and liquid and solid waste.

A waste-processing system 10 embodying the invention is illustrated in FIGS. 1-10. FIGS. 1-6 show the apparatus in which the process is conducted. The system 10 is described in terms of processing manure, but may also be used to process wood pulp, municipal wastes, or organic waste products in general.

FIG. 1 shows schematically the apparatus used to process high-solids farm waste. A digester enclosure 20 includes three major sections: a mixing chamber 30, a digester 40, and a clarifier 50. The digester enclosure 20 is arranged such that a relatively large digester 40 may be built in relatively small space.

FIG. 2 illustrates the construction of an outside wall 54 of the digester enclosure 20. The height of the outer wall 54 of the digester enclosure 20 is approximately 21 feet, with a liquid depth 58 in the digester enclosure 20 of approximately 18 feet and a biogas storage area 59 of about 18 inches above the liquid 58. A footing 62 provides an interface between the wall 54 and the ground 66, and supports the wall 54 and the edge 70 of the floor 74. Both the footing 62 and the wall 54 are constructed of poured concrete. The wall 54 is approximately twelve inches thick at the lower end 78 of the wall 54, and approximately eight inches thick at the upper end 82 of the wall. The floor 74 of the digester enclosure 20 is approximately three to five inches of concrete.

In another embodiment, insulation 86 with a thickness of approximately three-five inches may be arranged below the floor 74 and provides an interface between the floor 74 and the ground 66.

The roof 90 of the digester enclosure 20 is located approximately 15 feet, 8 inches above the floor 74 of the digester enclosure 20. The roof 90 is constructed of an approximately ten-inch thickness 98 of SPANCRETE concrete topped by a layer of insulation 94 with a thickness between four and eight inches, and more particularly, between three and four inches.

A bio gas storage chamber 102 may be located above the roof 90. The primary component of the chamber 102 is a liner 106 including an upper liner section 110 and a lower liner section 114. The liner 106 is preferably constructed from high-density polyethylene (HDPE), but may be any other suitable material. The liner 106 is sealed around the edges 118 of the liner 106 by capturing the edges 118 beneath six-inch channel iron 122, which is irremovably attached to the digester enclosure walls 54 using nuts 126 on a plurality of anchor bolts 130 embedded in the digester enclosure wall 54. A ten-inch PVC pipe 134 is inserted around the periphery of the chamber 102 within the liner 106 to assist in maintaining the seal around the periphery of the liner 106. The liner 106 is constructed such that it can flexibly fill with bio gas as the bio gas is produced in the digester 40, and can be emptied of bio gas as is needed. The bio gas storage chamber 102, as an addition to biogas storage 59 within the digester enclosure 20, may be replaced by any other suitable gas storage system including a roofed storage system.

Returning to FIG. 1, the mixing chamber 30 has horizontal dimensions of from approximately 32 feet to approximately 40 feet by approximately 15 to approximately 55 feet. Arranged within the mixing chamber 30 is approximately 2000 feet of three or four-inch black heating pipe 142, which is designed to carry hot water to heat sludge 144 within the mixing chamber 30. An influent pipe 148 carries manure 336 into the mixing chamber 30. The closed container may further include a heating device and may or may not include a partition. The heating device may comprise a conduit containing a liquid or gas with discharge nozzles to further agitate the waste material, positioned to heat waste material to form heated waste material. Mixing within the mixing chamber 30 is provided by at least one of a system of mixing nozzles utilizing re-circulated biogas or liquid and convective flow resulting from the heating of the manure 336 by the heating pipe 142. In one embodiment, the recirculation pipe may deliver effluent to the digester 166, in another embodiment to the mixing chamber 30. If required, a standard auger 146 used for removing solids from the mixing chamber 30 is arranged near the floor 150 of the mixing chamber 30 such that it can transport solids from the floor 150 of the mixing chamber 30 through the wall 154 of the mixing chamber 30 and to a collection device 158. The collection device 158 is optional. In another embodiment (not shown), solids may be removed from the mixing chamber 30 by any other suitable system, such as a sump pump.

Figure 3:
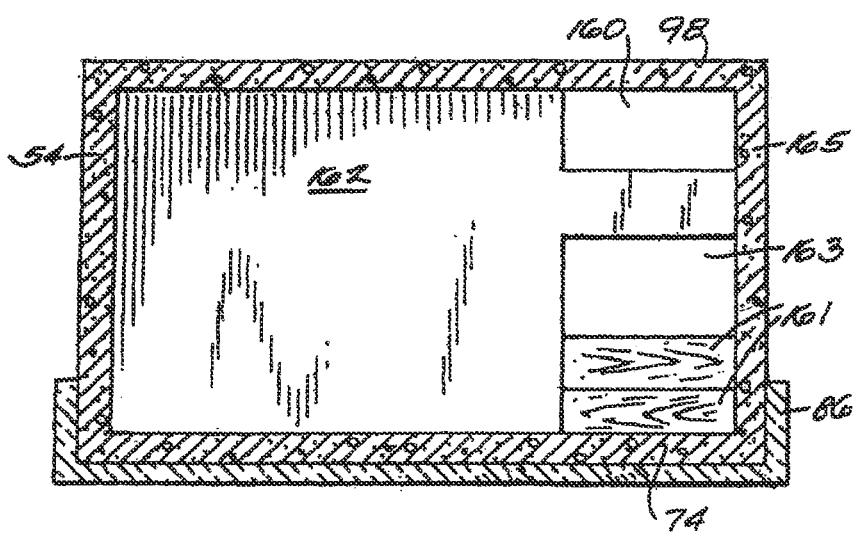
FIG. 3 is a cross-section elevational view of a wall between a mixing chamber and the digester and taken along the 3-3 line of FIG. 1.

As illustrated in FIG. 3, a cutout 160 formed in the wall 162 between the mixing chamber 30 and the digester 40 allows sludge to flow from the mixing chamber 30 into the digester 40. In addition, removable panels 161 may be positioned to block opening 163 in the wall 162. The removable panels shown in FIG. 3 are optional. Removable panels 161 may be removed as needed to allow greater flow from mixing chamber 30 to digester 40, if desired.

Returning to FIG. 1, the digester 40 is a generally U-shaped tank with overall horizontal dimensions of approximately 70-100 feet long and 60-80 feet wide. A center wall 165 approximately 90 feet in length divides the digester 40 into the two legs 166, 170 of the U-shape. Thus each leg 166, 170 of the digester 40 is approximately 100 feet long and 36 feet wide.

The first leg 166 of the digester 40 includes approximately 800 feet of three or four-inch black heating pipe 174 through which heated water or gas can flow. The heating pipe 174 is or separate gas pipes are arranged along the center wall 165. The second leg 170 of the digester 40 includes approximately 200 feet of four-inch black heating pipe 178, which is also arranged along the center wall 165. In another embodiment illustrated in FIG. 11, the heating pipes 174, 178 or separate gas pipes 178 may include jet nozzles 180 to dispense heated gas or recycled biogas into the sludge 144.

In addition to producing activated sludge 184, the anaerobic digestion of the digester 40 also produces bio gas in the form of methane gas, which is collected in the space above the liquid in digester 40 and below the roof 98 and can also be stored in the gas storage chamber 102. Any liquid that condenses within the chamber 102 is directed through the effluent pipe 196 (see FIGS. 7-9) to the liquid storage lagoon 198 (see FIGS. 7-9). The collected bio gas is used to fuel an internal combustion engine 138 (see FIG. 7) that, in combination with an electric generator, is used to produce electricity that is sold to a power utility 332 (see FIG. 7). The cooling system of the internal combustion engine 138 also produces hot coolant that is used for heating and agitation in the mixing chamber 30 and, alternatively, for heating and agitation in the mixing chamber 30 and digester 40. Hot water from the engine 138 passes through an air/water cooler 334 (see FIG. 7) to reduce the temperature of the water from approximately 180.degeree.F. temperature at the exit of the engine 138 to approximately 160° F. for use in the mixing chamber 30 and the digester 40.

Figure 4:
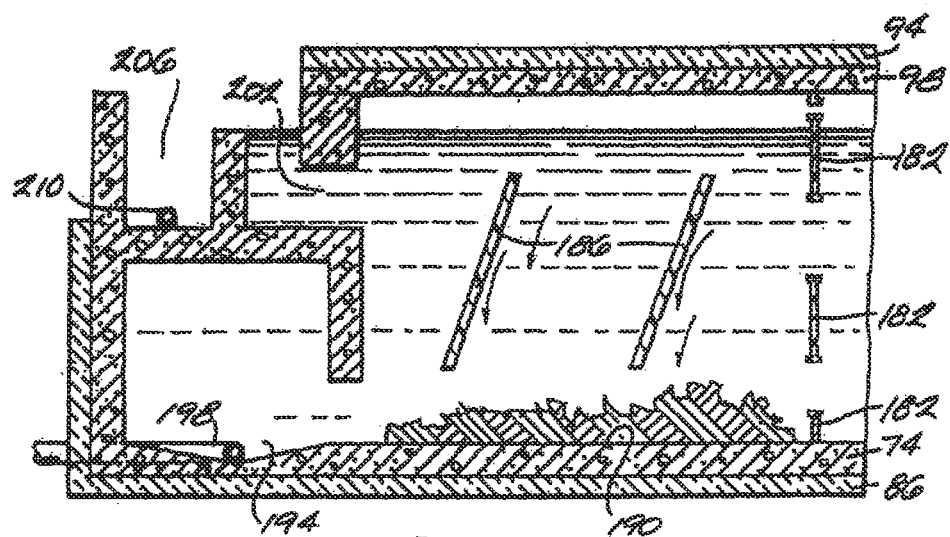
FIG. 4 is a partial cross-section elevational view of a clarifier, taken along the 4-4 line of FIG. 1.

As shown in FIG. 1, the optional clarifier 50 is located adjacent the digester 40 beyond clarifier panels 182 and adjacent the mixing chamber 30. The clarifier 50 has horizontal dimensions of approximately 36 feet by 21 feet, and is largely empty of any equipment or hardware, with the exception of an equipment room 183. Turning to FIG. 4, the clarifier panels 182 are constructed from HDPE and form a partial barrier between the digester 40 and the clarifier 50. The clarifier panels 182 cover the entire horizontal dimension across the clarifier 50 from the center wall 165 to outer wall 54. Separation panels 186 within the clarifier 50 serve to direct solids in a downward direction to the bottom 190 of the clarifier 50, where the solids collect in a sump 194. Sump pipe 198 leads to an standard solids press 214 (see FIGS. 7-9) and to the activated sludge recirculation pipe 147 carrying activated sludge 184 to the mixing chamber 30, or, alternatively, the digester 40 (see FIG. 1).

Figure 7:
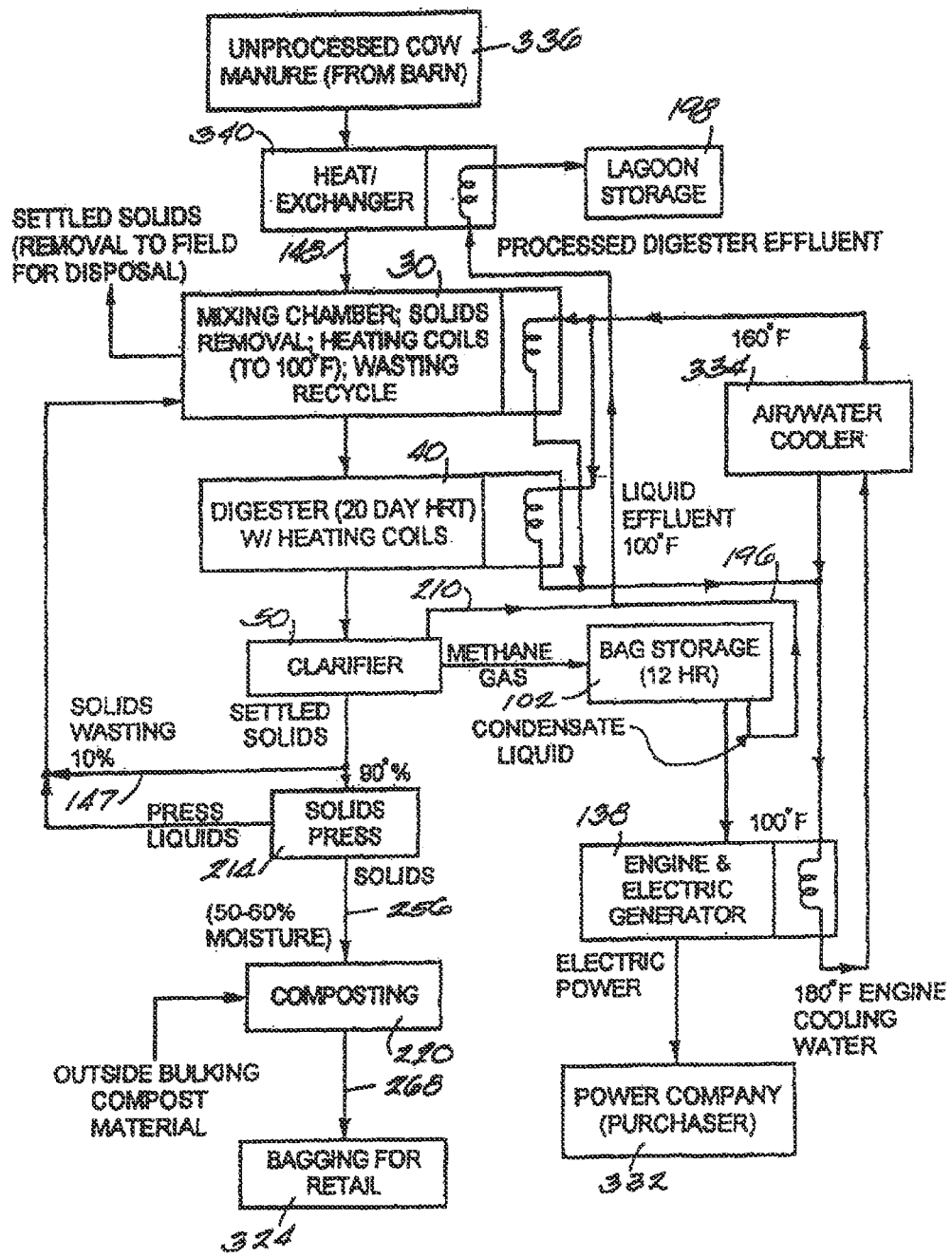
FIG. 7 is a flowchart of the process employed in the waste processing system shown in FIG. 1.
Figure 8:
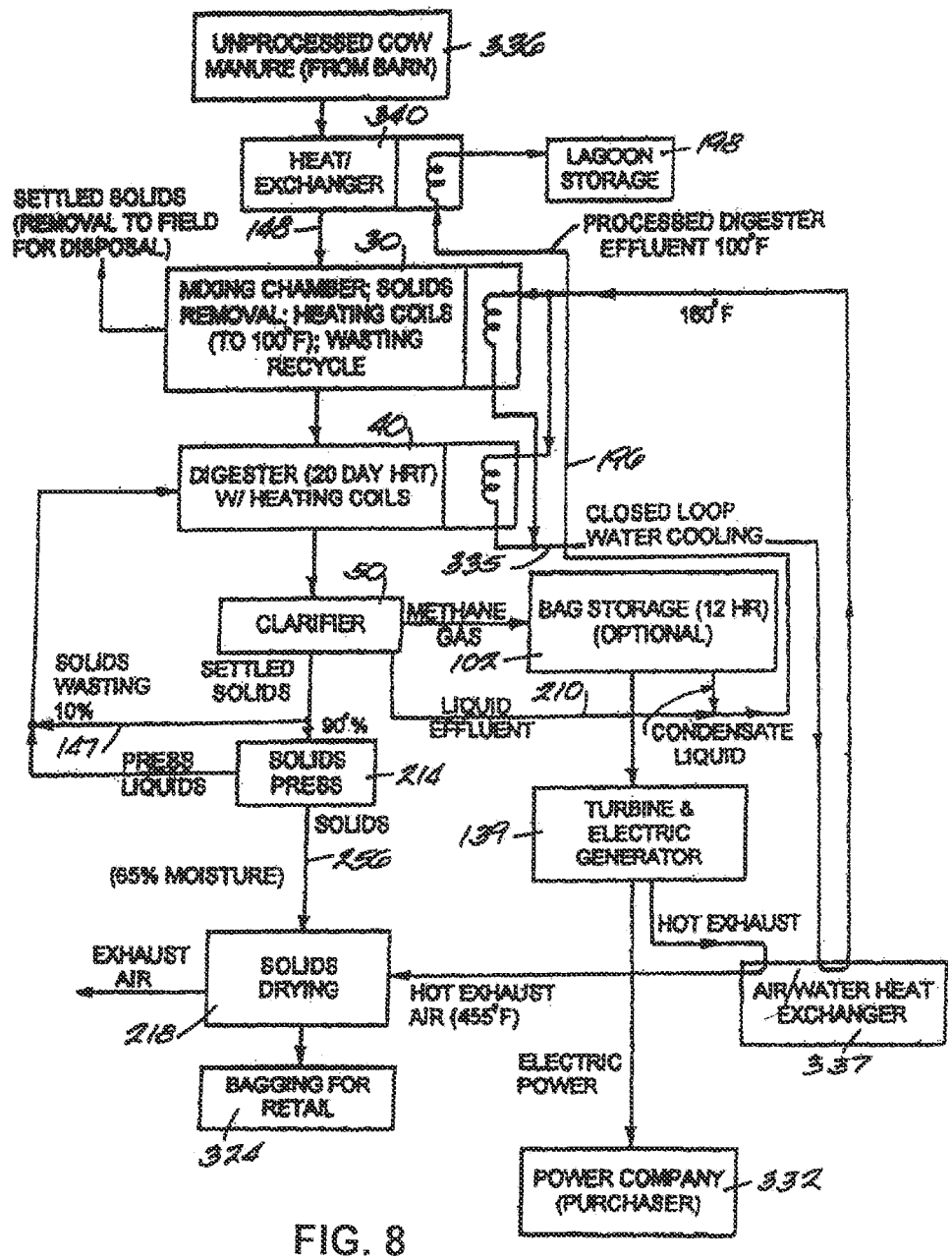
FIG. 8 is a view similar to FIG. 7 and shows an alternative process of the invention.
Figure 9:
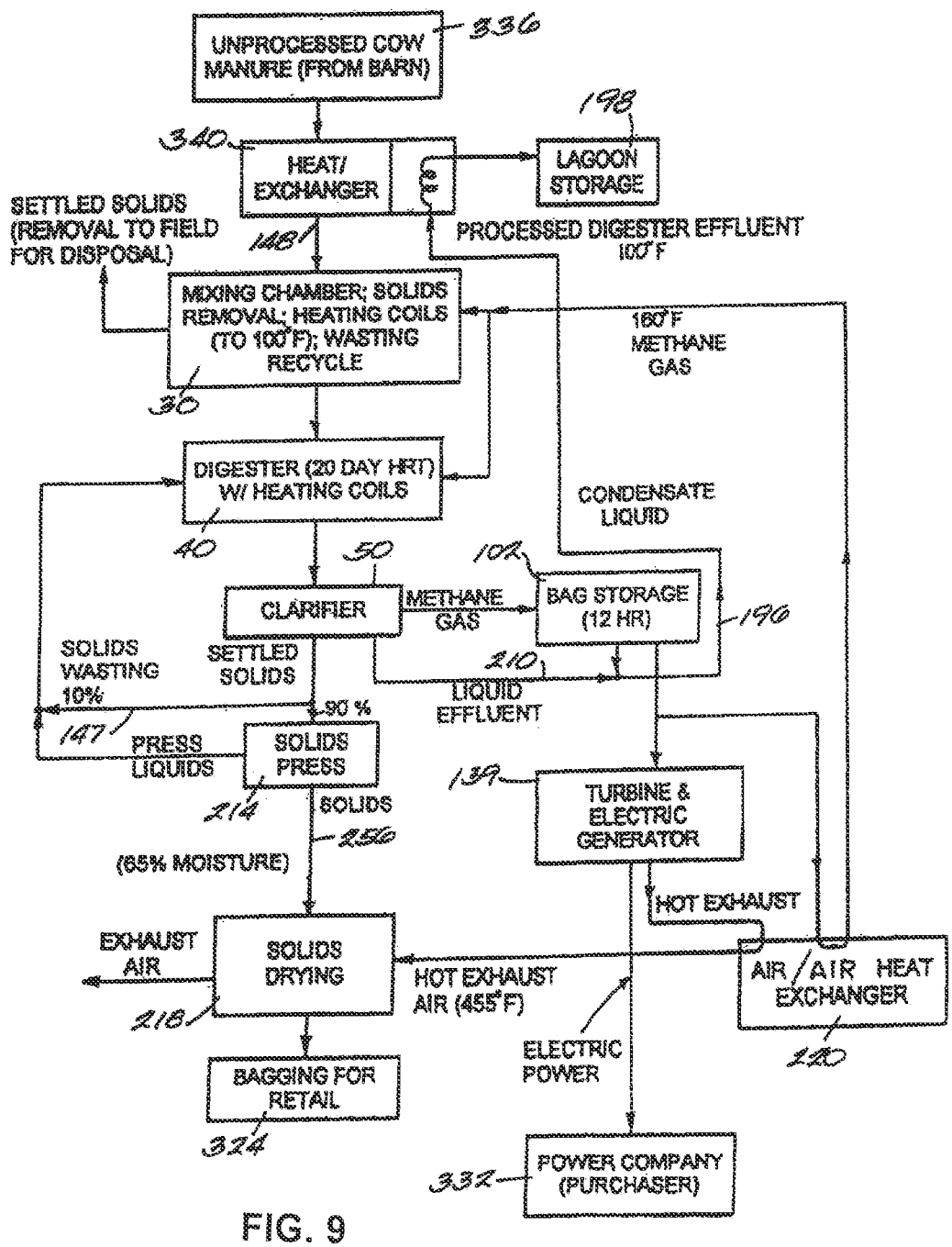
FIG. 9 is a view similar to FIGS. 7 and 8 and shows another alternative process of the invention.

As illustrated in FIGS. 7-9, a portion of the liquid produced as a result of the operation of the solids press 214 may be recycled to the mixing chamber 30 or the digester 40 for further processing.

Returning to FIG. 4, liquids in the clarifier 50 decant through gap 202 and collect in a liquid sump 206. A liquid effluent pipe 210 within the liquid sump 206 leads through a heat exchanger 340 (see FIG. 7) and to a liquid storage lagoon 198 (see FIG. 7).

Figure 6:
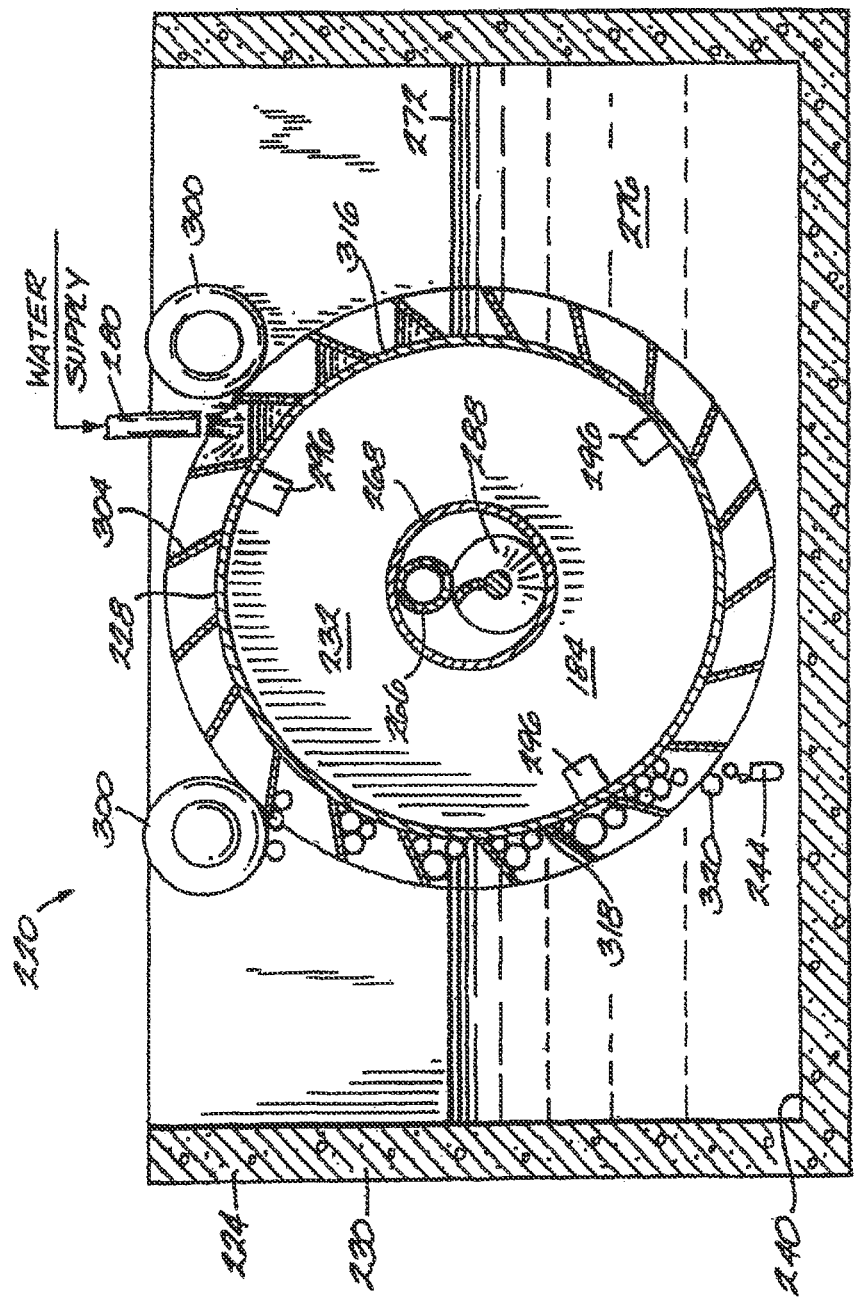
FIG. 6 is a cross-sectional view of the composter taken along the 6-6 line in FIG. 5.

A composter 220 as illustrated in more detail in FIGS. 5 and 6 is located downstream of the solids press 214. The composter is optional. The primary components of the composter 220 include a water tank 224 and a composting barrel 228. The water tank 224 is generally a rectangular parallelepiped with six-inch-thick walls 230 constructed from concrete. A four-inch layer of insulation 23 (not shown in FIG. 6) covers the periphery of the walls 230. A sump 236 is located in the floor 240 of the water tank 224. Extending through the floor 240 of the water tank 224 is an air supply pipe 244. A port 248 in the first wall 252 of the water tank 224 accommodates a sludge supply pipe 256 that connects the solids press 214 with the composter barrel 228. A port 260 in the second wall 264 of the water tank 224 accommodates a composter solids exit pipe 268.

The water level 272 of the water tank 224 may be varied to provide buoyant support to the composter barrel 228; the water level 272 as illustrated in FIGS. 4 and 6 is representative of a typical level. The water 276 is typically at 140-160° F. A water inlet pipe 280 provides a flow of water 276 to the composter barrel 228 and the water tank 224. The water 276 is supplied from the cooler 334 of engine 138.

The composter barrel 228 defines an interior chamber 232. A sludge supply auger 284 is located within the sludge pipe 256 and extends from within the sludge supply pipe 256 into chamber 232 of the barrel 228. A composted solids exit auger 228 extends from within chamber 232 of barrel 228 into the composter solids exit pipe 268. Each pipe 256, 268 is connected to the ends 292, 294 of the composter barrel 228 using a double rotating union seal with an internal air pressure/water drain (not shown). The pipes 256, 268 and augers 284, 288 are designed such that air that is necessary for drying the sludge and for aerobic digestion may pass through the composter barrel 228. Air passes through solids exit pipe 268 and air inlet pipe 266, into the composter barrel 228, and out through air outlet pipe 258 and sludge supply pipe 256. The air pipes 258, 266 extend vertically to keep their ends 270 above the activated sludge 184 in the composter barrel 228.

The composter barrel 228 is generally cylindrical and approximately 100 feet long and 10 feet in diameter. A plurality of wear bars 296 is attached to the exterior circumference of the barrel 228. Rubber tires 300 acting on the wear bars 296 serve to hold the composter barrel 228 in position.

Another embodiment is illustrated in FIGS. 5 and 6. A plurality of vanes 304 is attached to barrel 228. These vanes 304 extend between the third and fourth wear bars 308, 312. The vanes 304 are generally parallel to the longitudinal axis of the composter barrel 228. As shown in FIG. 6, to effect cooperation with the vanes 304, the water inlet pipe 280 and the air inlet pipe 244 are laterally offset in opposite directions from the vertical centerline of the composter barrel 228. As a result, when water 276 flows from the water inlet pipe 280, the water 276 collect on the vanes 304 on a first side 316 of the composter barrel 228, and when air 320 flows from the air inlet pipe 244, air 320 collects under the vanes 304 on a second side 318 opposite the first side 316 of the composter barrel 228. The lateral imbalance resulting from weight of water 276 on the first side 316 of the barrel 228 and the buoyancy of the air 320 on the second side of the barrel 228 causes of the barrel 228 to rotate in a clockwise direction as viewed in FIG. 6.

The composter barrel 228 is slightly declined toward the exit end 294 of the composter barrel 228 to encourage the activated sludge 184 within the composter barrel 228 to move along the longitudinal axis of the composter barrel 228 toward the exit end 294. As shown in FIG. 6, the composter barrel 228 also includes internal baffles 296 that serve to catch and turn the activated sludge 184 as the composter barrel 228 rotates.

As illustrated in FIG. 1, the composter solids exit pipe 268 connects to a standard bagging device 324 that places the composted solids into bags 328 for sale.

In operation of the waste-processing system 10, as illustrated in FIGS. 1 and 7, unprocessed cow manure 336 from area farms and other sources is transported to the waste processing site and transferred to a heat exchanger 340 where, if necessary, the manure 336 is thawed using warm water from the clarifier 50 by way of liquid effluent pipe 210.

Manure 336 is then transferred from the heat exchanger 340 to the mixing chamber 30 through influent pipe 148, where the manure 336 may, alternatively, be mixed with activated sludge 184 recycled from the clarifier 50 by way of activated sludge recirculation pipe 147 to become sludge 144. The sludge 144 is heated to approximately 95-130° Fahrenheit by directing coolant at approximately 160° F. from the engine cooler 334 through the mixing chamber heating pipes 142. In addition, if required, solids such as grit fall to the bottom of the mixing chamber 30 under the influence of gravity and are removed using the mixing chamber auger 146. The solids are then transferred to a disposal site.

In another embodiment, an access port vacuum can be used.

After a stay of approximately one day in the mixing chamber 30, the sludge 144 flows through cutout 160 or opening 163 in the wall 162 and into the digester 40, where anaerobic digestion takes place. The activated sludge 184 added to the manure 336 in the mixing chamber 30 or digester 40 serves to start the anaerobic digestion process.

The apparatus and method described herein employ modified plug flow or slurry flow to move the sludge, unlike the plug flow in prior art systems. The digester heating pipes 174, 178 locally heat the sludge 144 using hot water at approximately 160° F. from the cooler 334 of the engine 138, causing the heated mixed sludge to rise under convective forces. The convection develops a current in the digester 40 that is uncharacteristic of prior are high-solids digesters. Sludge 144 is heated by the digester heating pipes 174, 178 near the digester center wall 165, such that convective forces cause the heated sludge 144 to rise near the center wall 165. At the same time, sludge 144 near the relatively cooler outer wall 54 falls under convective forces. As a result, the convective forces cause the sludge 144 to follow a circular flow path upward along the center wall 165 and downward along the outer wall 54. At the same time, the sludge 144 flows along the first and second legs 166, 170 of the digester 50, resulting in a combined corkscrew-like flow path for the sludge 144.

In another embodiment (not shown), hot gas injection jets using heated gases from the output of the engine 138 replace the hot water digester heating pipes 174, 178 as a heating and current-generating source. The injection of hot gases circulates the sludge 144 through both natural and forced convection. A similar corkscrew-like flow path is developed in the digester 40.

As shown in FIG. 11, to further increase upward flow of the heated sludge 14 near the center wall 165, biogas may be removed from the biogas storage area 59 in the digester 40, pressurized with a gas centrifugal or rotary-lobe blower, and injected into the heated sludge 144 through nozzles 376 positioned onto conduit 378. This recycled biogas injection near the floor 74 of the digester 40 serves to increase the rapidity of the cork-screw-like flow path for the heated sludge 144.

In the arrangement shown in FIG. 1, the U-shape of the digester 40 results in a long sludge flow path and thus a long residence time of approximately twenty days. As the sludge 144 flows through the digester 40, anaerobic digestion processes the sludge 144 into activated sludge 184. The anaerobic digestion process also reduces the phosphate content of the liquid effluent after solids removed, by approximately 30-50 percent for dairy waste, which is a key factor in meeting future environmental regulations. In yet another embodiment, anaerobic digestion process reduces the phosphate content of the liquid effluent after solids removal, by approximately 30-35 percent for poultry waste and by approximately 30-50% for waste from hogs.

From the digester 40 the activated sludge 184 flows into the optional clarifier 50. The clarifier 50 uses gravity to separate the activated sludge 184 into liquid and solid portions. Under the influence of gravity and separation panels 186, the liquid portion rises to the top of the mixture and is decanted through a gap 202 into a liquid sump 206. It is later transferred to a lagoon storage 198 through effluent pipe 210. The liquid is then taken from the lagoon 198 for either treatment or use as fertilizer.

The solid portion of the activated sludge 184 settles to the bottom 190 of the clarifier 50 in sump 194. From there, approximately ten to twenty-five percent of the activated sludge 184 is recycled to the digester 40 or mixing chamber 30 through activated sludge recirculation pipe 147 to mix with the incoming manure 336, as described above. The remaining approximately seventy-five to ninety percent of the activated sludge 184 is removed from the clarifier 50 through sump pipe 198 and is transferred to the solids press 214 in which the moisture content of the activated sludge 184 is reduced to approximately 65-75 percent. Paper mill sludge likely will retain more moisture, and thus, the moisture content may be reduced to approximately 70-80 percent.

From the solids press 214, the activated sludge 184 is transferred through sludge supply pipe 256 using sludge supply auger 284 to the interior chamber 232 of the composter barrel 228 where the activated sludge 184 is heated and agitated such that aerobic digestion transforms the activated sludge 184 into usable fertilizer. Outside bulking compost material can be added to the chamber 232 to make the fertilizer more suitable for later retail sale. As the composter barrel 228 turns, baffles 296 within the chamber 232 agitate and turn the sludge. This agitation also serves to aerate the sludge to enhance aerobic digestion. At the same time, the tank of water 224 in which the barrel 228 sits heats the barrel 228. This heating also promotes aerobic digestion.

In the preferred embodiment, water 276 falling from the water inlet pipe 280 and air 320 rising from the air inlet pipe 244 collects on the vanes 304 and causes the composter barrel 228 to turn around its longitudinal axis. In other embodiments, direct motor or belt drives, or any other suitable drive mechanism may turn the composter barrel 228.

As the activated sludge 184 turns over and undergoes aerobic digestion in the chamber 232, it also travels longitudinally and eventually exits the composter barrel 228 through the composter solids exit pipe 268, driven by the composter solids exit auger 288. The processed sludge, which has become usable fertilizer at approximately forty-percent moisture, is transferred to a bagging device 324. In the bagging device 324, the processed sludge is bagged for sale as fertilizer.

In an alternative embodiment illustrated in FIG. 8, a turbine 139 replaces the internal combustion engine as described above. The turbine 139 can be any turbine engine including but not limited to an AlliedSystems TURBOGENERATOR turbine power system. The turbine 139 is fueled by the methane collected in the bio gas storage chamber 59 or 102. The difference with the use of a turbine 139 from the previously-discussed process are outlined as follows. Instead of an engine cooler 334 producing heated coolant, the turbine 139 produces exhaust gases at approximately 455.degree.F. The hot exhaust gases are used to heat water in a closed loop 335 through an air/water heat exchanger 337. The heated water is then used for heating in the mixing chamber 30 and for heating and agitation in the digester 40. This embodiment is used in conjunction with a composter (not shown) as described above.

As shown in FIG. 8, the composter is replaced with a solids dryer 218 in which hot exhaust from the turbine 139 or reciprocating engine 138 is used to dry the sludge taken from the solids press 214. From the solids dryer 218, the activated sludge 184 is transferred to a bagging device 324. In the bagging device 324, the processed sludge is bagged for sale as fertilizer.

In another embodiment illustrated in FIG. 9, hot exhaust gases from the turbine 139 are used to heat methane from the bio gas storage chamber 102 to approximately 160° F. in an air/air heat exchanger 220. The heated methane is then injected into the mixing chamber 30 and the digester 40 for heating and agitation. In this embodiment, it is possible to seal off the digester 40 from any air contamination because only methane is used for heating and agitation. The methane is then recaptured in the bio gas storage chamber for reuse. This embodiment is used in conjunction with a composter (not shown) as described above.

In the embodiment illustrated in FIG. 9, the composter is replaced with a solids dryer 218 in which hot exhaust from the turbine 139 is used to dry the sludge taken from the solids press 214. Again, from the solids dryer 218, the activated sludge 184 is transferred to a bagging device 324. In the bagging device 324, the processed sludge is bagged for sale as fertilizer.

Figure 10:
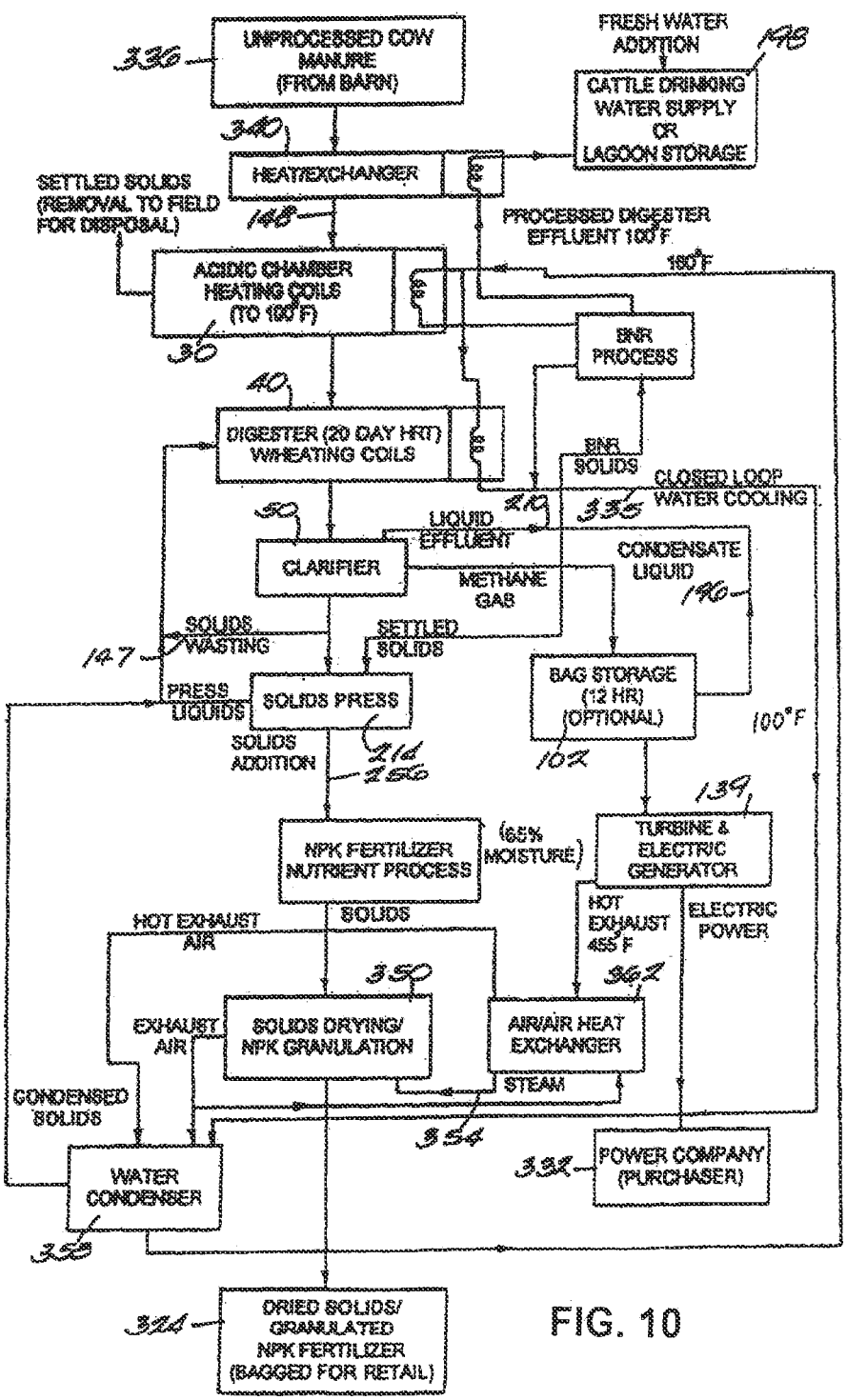
FIG. 10 is a view similar to FIGS. 7-9 and shows another alternative process of the invention.

In still another embodiment illustrated in FIG. 10, a fluidizing bed dryer 350 takes the place of the composter or solids dryer described in previous embodiments. Pressed bio solids at approximately 35 percent solids from the solids press 214 enter the fluidizing bed dryer 350 where the solids are fluidized using heated air in a closed-loop air system 354. This fluidizing results in moisture from the bio solids being entrained in the heated air. The moisture-laden heated air passes through a water condenser 358 where water is removed from the heated air and circulated back to the heating pipe 142 in the mixing chamber 30 and to the heating pipe 174 in the digester 40. Heat is provided to the closed-loop air system 354 through an air/air heat exchanger 362. Hot exhaust gases from a series of turbines 139 provide heat to the air/air heat exchanger 362. The exhaust gases then enter the water condenser 358 to remove combustion moisture from the turbine exhaust before the remaining gases are vented to the atmosphere. The water condenser 358, in addition to recapturing water, also recaptures heat carried by the turbine exhaust and by the heated air in the closed-loop air system 354. This recaptured heat is used to heat the water circulating in the closed-loop water heating system.

The combination of a fluidizing bed dryer 350 and an air/air heat exchanger 362 recaptures heat produced by the turbines 139 that would otherwise be lost in the turbine exhaust. The heated air in the fluidizing bed dryer 350 evaporates water carried in the effluent from the solids press. The latent heat of vaporization carried by the moisture in the air leaving the fluidizing bed dryer 350 is substantially recaptured in the water condenser 358. The closed-loop air system 354 allows for air with reduced oxygen content to be used in the fluidizing bed dryer 350 to reduce the risk of fire associated with drying organic material. In addition, the closed-loop air system 354 allows for the addition of an auxillary burner (not shown) if needed to process wetter material in the fluidizing bed dryer 350. A variable speed fan (not shown) can be added to the closed-loop air system 354 after the water condenser 358 to pressurize the air for the fluidizing bed dryer 350.

In the embodiment illustrated in FIG. 10, from the solids dryer 218, the activated sludge 184 is transferred to the bagging device 324. In the bagging device 324, the processed sludge is bagged for sale as fertilizer.

In another embodiment (not shown), the composter is replaced with a solids dryer 218 in which hot exhaust from the internal combustion engine 138 is used to dry the sludge taken from solids press 214. Again, from the solids dryer 218, the activated sludge 184 is transferred to a bagging device 324. In the bagging device 324, the processed sludge is bagged for sale as fertilizer.

Figure 12:
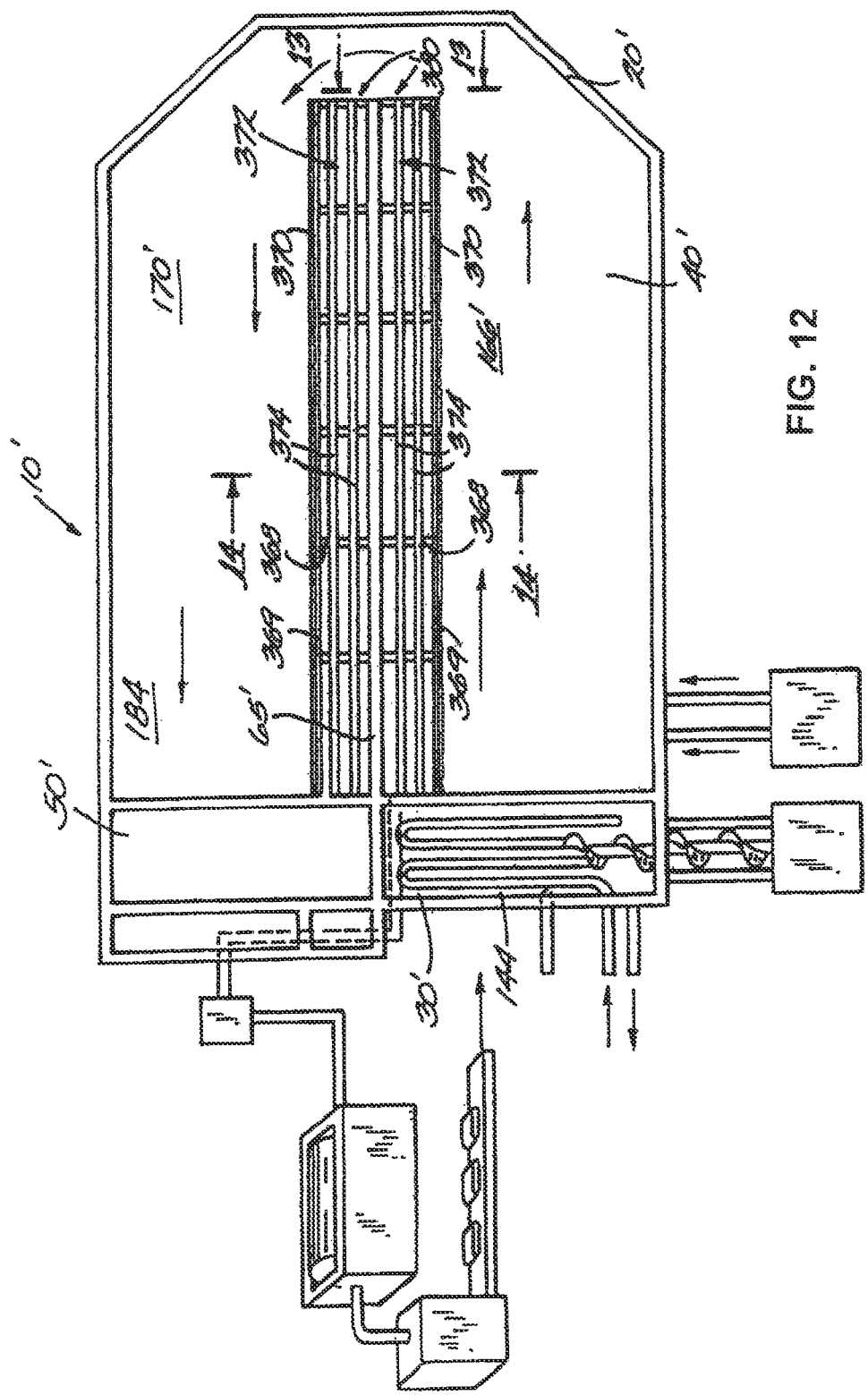
FIG. 12 is a schematic view of an alternative waste processing system embodying the invention.

FIG. 12 illustrates another embodiment of the waste processing system of the present invention, wherein like elements have like numerals. Specifically, FIG. 12 illustrates a waste processing system 10', which includes a digester enclosure 20', a mixing chamber 30', a digester 40' and a clarifier 50'. A center wall 65' divides the digester 40' into a first leg 166' and a second leg 170'. The sludge 144 can therefore move from the mixing chamber 30' into the digester 40' along the first leg 166' in a first direction, and toward the clarifier 50' along the second leg 170' of the digester 40' in a second direction opposite the first direction.

The first leg 166' and the second leg 170', as illustrated in FIG. 12, each include a partition 370 positioned relative to the center wall 65' such that a space 380 is created between the partition 370 and the center wall 65'. The partition may comprise at least one of a rigid board or plank, curtain or drape, tarp, film, and a combination thereof. In addition, the partition may be constructed of a variety of materials, including without limitation, at least one of a metal, wood, polymer, ceramic, composite, and a combination thereof. The first leg 166' and the second leg 170' each further include a heating device 372 positioned within the space 380 between the partition 370 and the center wall 65' such that sludge 144 or activated sludge 184 (referred to from this point forward as sludge 144 for simplicity) is heated as it contacts the heating device 372. Heated sludge 144 rises relative to cooler sludge 144 by free convection and is allowed to rise upwardly within the space 380.

Figure 13:
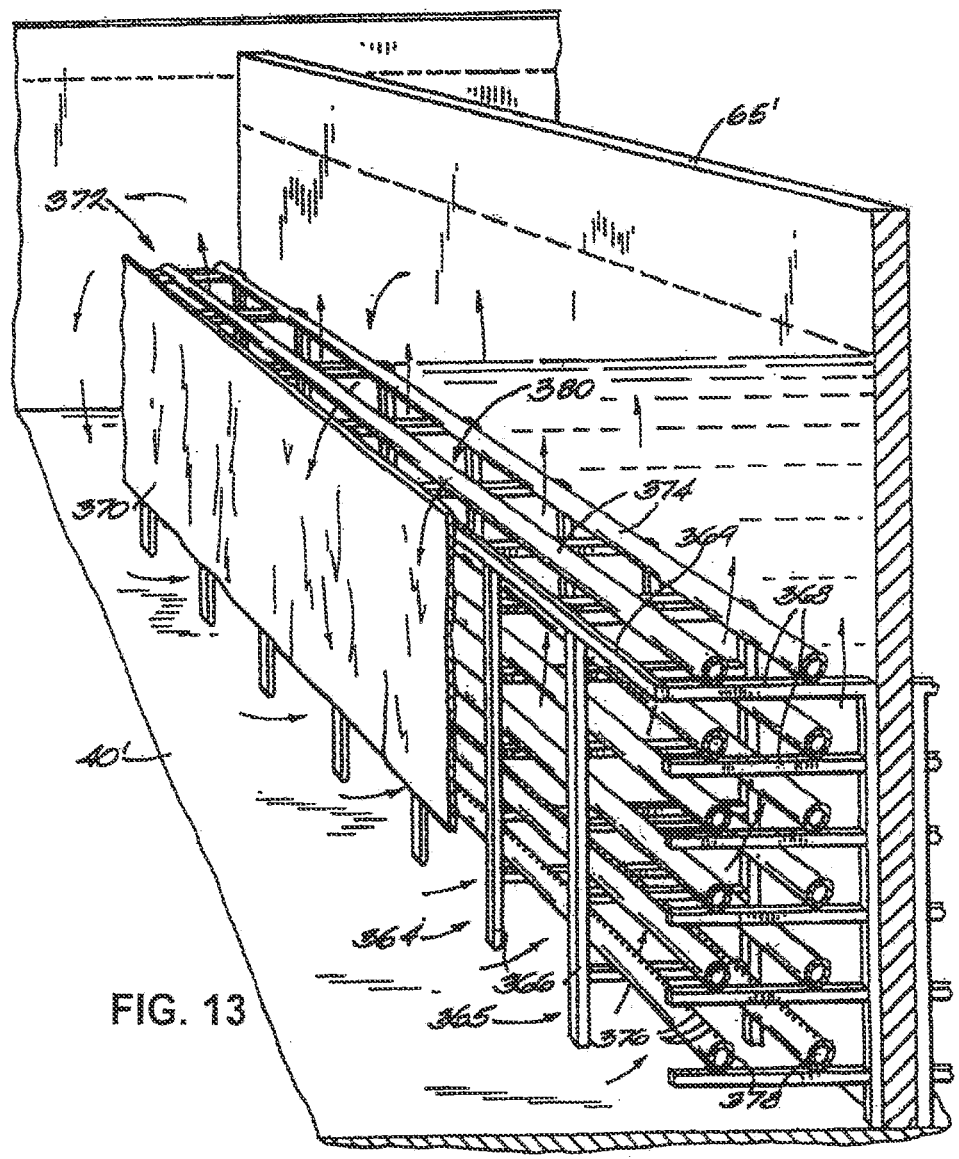
FIG. 13 is a partial cross-sectional view of a digester taken along the 13-13 line in FIG. 12.
Figure 14:
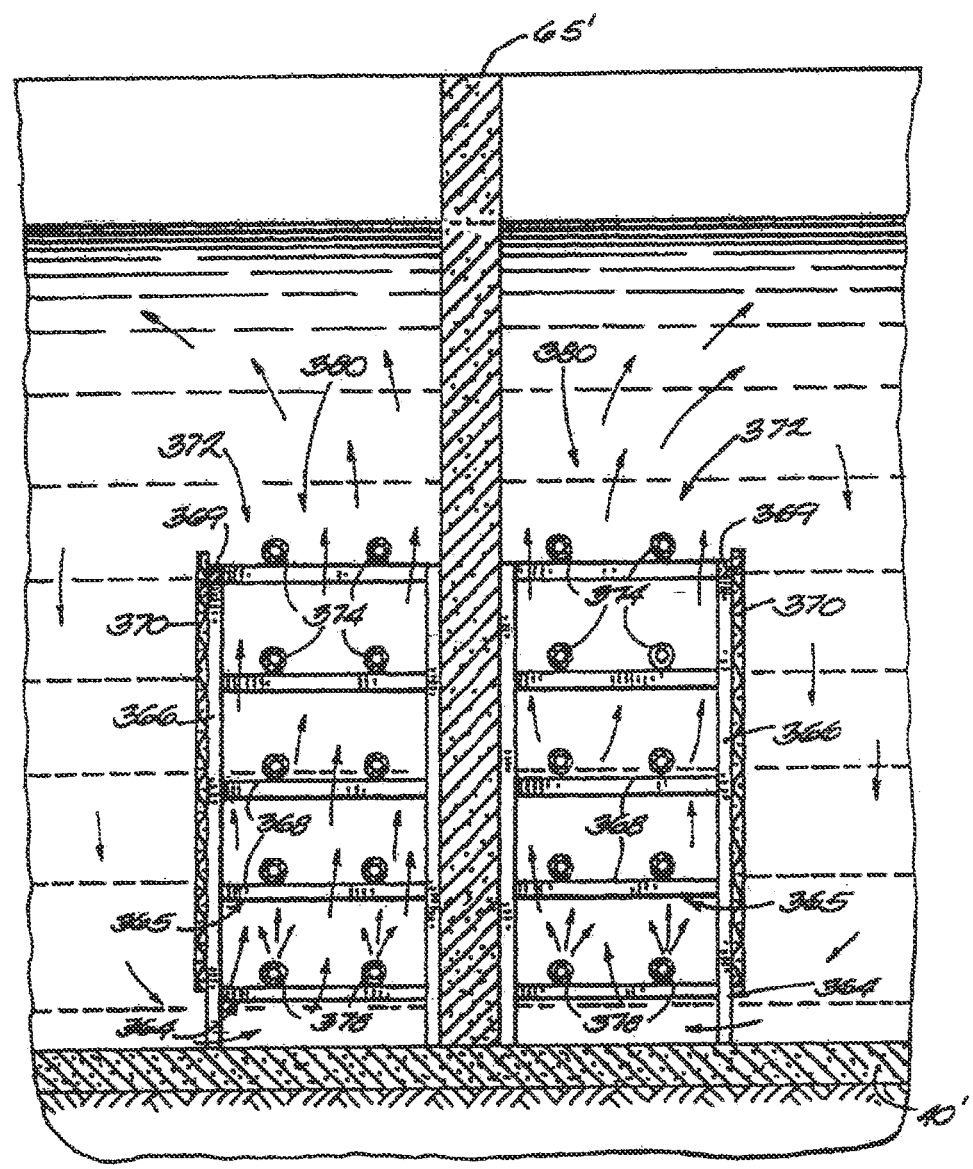
FIG. 14 is a partial cross-section elevational view of the digester taken long the 14-14 line in FIG. 12.

The heating device(s) 372 and the partition(s) 370 are shown in greater detail in FIGS. 13 and 14. For simplicity, one of the heating devices 372 and the partitions 370 will be described in greater detail, but it should be noted that the description may equally apply to the other heating device 372 and partition 370. As shown in FIGS. 13 and 14, the heating device 372 includes a series of conduits 374, each containing a heating medium. A variety of heating media may be used with the present invention, including at least one of water and a gas. The conduits 374 do not all need to contain the same heating medium. That is, some of the conduits 374 may contain a gas, while others contain a liquid, such as water.

As illustrated in FIGS. 13 and 14, the waste processing system 10' may further include at least one conduit 378, which contains a compressed, recycled biogas from the biogas storage area 57 and has nozzles 376. The nozzles 376 are gas outlets. The compressed biogas contained in the conduit 378 flows through the conduit 378 and out the nozzles 376, such that as the gas escapes the conduit 378 via the nozzles 376, the gas is propelled upwardly in the space 380 to promote the sludge 144 to move upwardly through the principle of air/water lifting. FIGS. 13 and 14 illustrate two conduits 378 having nozzles 376. Any number of conduits 378 having nozzles 376 can be used without departing from the spirit and scope of the present invention. The nozzles 376 may be simple holes drilled into conduit 378 or may be specialized nozzles 376 attached to conduit 378 via welding or tapping.

Referring to FIGS. 13 and 14, a frame 364 is positioned within the space 380 to support the heating device 372 and the conduits 378. The frame 364 is illustrated as comprising a plurality of ladder-like units 265 and a connecting bar 369 running generally parallel to the center wall 65' to connect the units 365. Each unit 365, as illustrated in FIGS. 13 and 14, is formed of two vertical columns 366 positioned on opposite sides of the space 380 and a plurality of crossbeams 368 connecting the two vertical columns 366 across the space 380. The frame 364 is illustrated by way of example only, and the present invention is in no way limited to the illustrated support structure. A variety of frame elements can be used to support the heating device 372, conduits 378, and/or other components of the waste processing system 10' within the space 380 without departing from the spirit and scope of the present invention.

As illustrated in FIGS. 13 and 14, the partition 370 has a top edge 371 and a bottom edge 373. In addition, the illustrated partition 370 is substantially vertical and shorter in height than the digester 40', such that heated sludge 144 can move over the top edge 371 of the partition 370 and out of the space 380 between the partition 370 and the center wall 65', and cooled sludge 144 can move under the bottom edge 373 of the partition 370 and into the space 380. Therefore, as illustrated by the arrows in FIGS. 13 and 14, the partition 370, in conjunction with the heating device 372, promotes upward and downward movement of the sludge 144. This upward and downward movement of the sludge 144 results in an overall spiral movement of the sludge 144 as the sludge 144 is moved along the first and second legs 166', 170' of the digester 40'. Further promoting this spiral motion are the two conduits 378 with nozzles 376, which are located beneath the series of conduits 374 of the heating device 372 in FIGS. 13 and 14. The spiral motion of the sludge 144 throughout the digester 40' promotes thermal mixing of the sludge 144 to produce activated sludge 184.

The series of conduits 374 illustrated in FIGS. 12-14 is formed by having a two-by-five configuration within the space 380 (i.e. two conduits 374 across and five conduits 374 up and down), with the conduits 374 running generally parallel to the center wall 65'. Another example is a two-by-six configuration, as shown in FIG. 13. In another embodiment, a single row of conduits, one conduit 374 across and five or six conduits 374 up and down.

In addition, two conduits 378 having nozzles 376 also run generally parallel to the center wall 65' and are positioned beneath the series of conduits 374 just described. It should be noted, however, that any number of conduits 374 containing heating medium, and any number of conduits 378 having nozzles 376 arranged in a variety of configurations can be used without departing from the spirit and scope of the present invention. The series of conduits 374 and the conduits 378 having nozzles 376 depicted in FIGS. 12-14 are shown by way of example only.

In yet another embodiment, the invention relates to methods and apparatuses for the anaerobic digestion of waste material to produce biosolids that meet the requirements of Class A biosolids.

Figure 15:
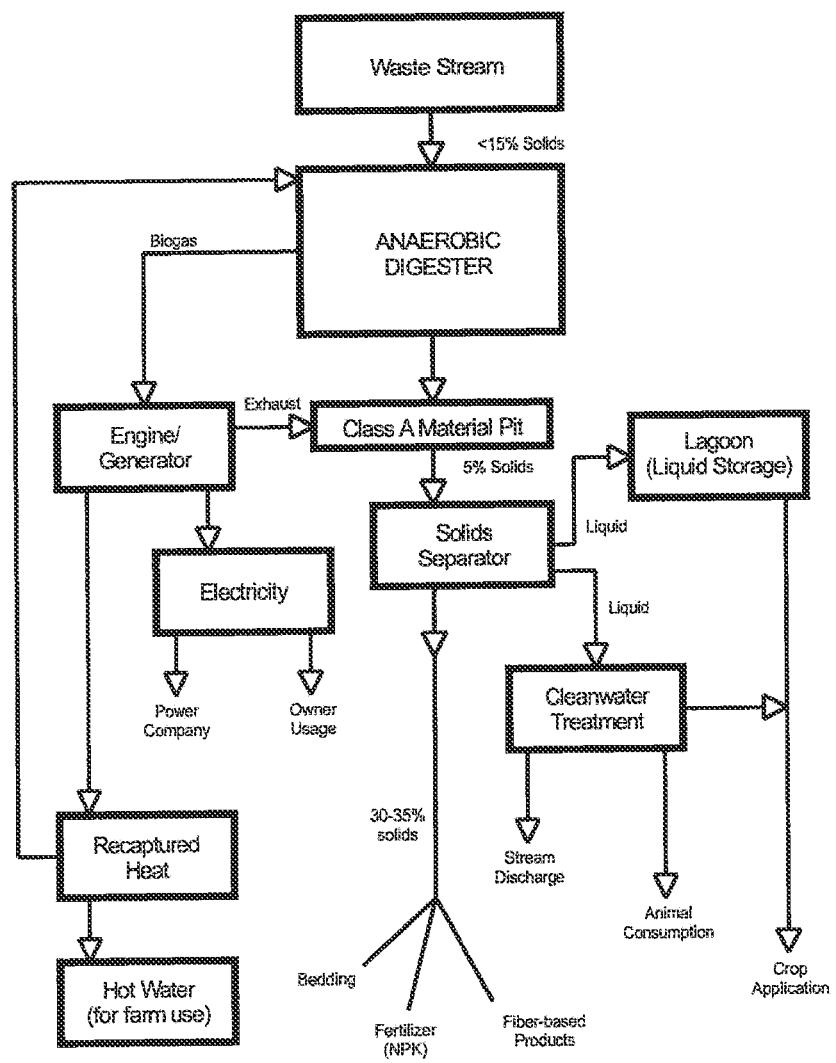
FIG. 15 is a flowchart depicting a waste processing system to produce biosolids with fecal coliform densities less than 1,000 Most Probable Number (MPN) per gram total solids (dry weight density).

One representative example of a method of anaerobic digestion yielding Class A biosolids is depicted in FIG. 15. Waste material, such as material from a waste stream, is placed into an anaerobic digester, where the waste material is heated to a specific temperature and for a specified period of time. The material can be heated to a mesophilic temperature range of 15-40° C. (77-104° F.) or a thermophilic temperature of 41-80° C. (113-176° F.).

Digestion of waster material in the anaerobic digester produces biogas that can be used to power an engine/generator and produce electricity that can be used to power equipment on the premises or sold to a power company. Recaptured heat from the engine/generator can be circulated back to the anaerobic digester or used to heat water and produce hot water for use on the premises of the digester.

The digested waste material is then moved into a Class A material pit (heating pit), where the material is heated to a suitable temperature to produce Class A biosolids including but not limited to 140, 141, 142, 143, 144, 145, 146, 147, 148, 148, 150, 151, 152, 153, 154, 155, 156, 157, 158, 159, 160-170, 170-180, 180-190, 190-200, and greater than 200° F.

In one embodiment, the waste material is transferred from the Class A material pit (heating pit) to a solids separator, wherein the solid waste is separated from the liquid fraction. The solids material can be used for bedding, fertilizer, and fiber based products. The liquid fraction can be treated to produce liquid for stream discharge or liquid for animal consumption. The liquid fraction also can be stored in a lagoon and used for crop application.

In yet another embodiment, a method for producing Class A biosolids is disclosed comprising: placing unprocessed waste material in a mixing chamber of a digester, wherein said mixing chamber comprises heating coils that can heat at least to 100° F.; removing solid particulates from the floor of the mixing chamber; digesting the waste material for a specified period of time in the main vessel; heating the digested waste material in a heating pit, wherein the waste material reaches a desired temperature; plug-flowing the waste material through the heating pit over the weir wall into the effluent pit; collecting the solid and liquid waste in an effluent pit; and separating the solids from the liquid.

In another embodiment, the unprocessed waste material can be any waste material including but not limited to wood, grass, agricultural residue, manure, recycled waste paper, and agricultural waste materials. Examples of sources of waste material include, but are not limited to, livestock production facilities, such as cattle, swine, goat, sheep, dairy cow, horse and the like, chicken ranches, turkey farms, duck farms, geese farms, human waste, and the like. Waste material may be collected using any suitable means in the art.

There are a myriad of anaerobic digester systems. Maintaining higher constant temperature reduces reactor volumes required to treat and stabilize waste. A conventional anaerobic digester system generally includes the following components: manure transfer and mixing pit, a digester made of steel, fiberglass, concrete, earth or other suitable material (including heating and mixing equipment if needed), biogas handling and transmission, and gas end use (combustion) equipment such as electric generation equipment.

Conventional anaerobic digesters also can require significant operational oversight depending on operational mode and temperature. Conventional anaerobic digester systems also require proper design and sizing to maintain critical bacterial populations responsible for waste treatment and stabilization for sustained long-term predictable performance. Sizing requirements are based on hydraulic retention time (HRT), and loading rate where the operating temperature affects these sizing parameters. These factors (size, materials, operational requirements) affect digester costs, which may be fairly capital intensive and in some economies and farm scales may not be affordable or may be inoperable if experienced technicians are not available.

In one embodiment, anaerobic digesters having any type of process configuration can be used including, but not limited to batch, continuous, mesophilic temperature, thermophilic temperature, high solids, low solids, single stage complexity and multistage complexity.

In another embodiment, a batch system of anaerobic digestion can be used. Biomass is added to the reactor at the start of the process in a batch and is sealed for the duration of the process. Batch reactors suffer from odor issues that can be a severe problem when they are emptied. Typically biogas production will be formed with a normal distribution pattern over time. The operator can use this fact to determine when they believe the process of digestion of the organic matter has completed.

In yet another embodiment, a continuous system of anaerobic digestion can be used. In continuous digestion processes, organic matter is typically added to the reactor in stages. The end products are constantly or periodically removed, resulting in constant production of biogas. Examples of this form of anaerobic digestion include, continuous stirred-tank reactors (CSTRs), Upflow anaerobic sludge blanket (UASB), Expanded granular sludge bed (EGSB) and Internal circulation reactors (IC).

In yet another embodiment, the heating coils of the mixing chamber can comprise nozzles to allow for recycled biogas to mix the components of the mixing chamber. The mixing chamber can comprise heating coils that can heat at least to 100° F.

The waste material can be anaerobically digested for any desired period of time including 5-10, 10-15, 16, 17, 18, 19, 20, 21, 22, 23, 24, 25, 26, 27, 28, 29, 30, and greater than 30 days of hydraulic retention time ("HRT").

Following digestion for the appropriate period of time to achieve the desired result, the waste material is heated in a heating pit at a temperature necessary to produce Class A biosolids. The waste material can be heated to any temperature including but not limited to 140, 141, 142, 143, 144, 145, 146, 147, 148, 149, 150, 151, 152, 153, 154, 155, 156, 157, 158, 159, 160-170, 170-180, 180-190, 190-200, and greater than 200° F.

After heating the waste material in the heating pit, the material is plug-flowed over a separation weir wall into an effluent pit. The solids and liquid in the effluent pit are then separated. In another embodiment, the method further comprises collecting the liquid waste material in an effluent pit, wherein the effluent pit comprises heat racks to acquire the surplus heat. The collected heat then is used to heat the liquid waste. The liquid waste can be heated to any desired temperature including but not limited to 140, 141, 142, 143, 144, 145, 146, 147, 148, 149, 150, 151, 152, 153, 154, 155, 156, 157, 158, 159, 160-170, 170-180, 180-190, 190-200, and greater than 200° F.

In still yet another embodiment, the method further comprises pressing the solid waste material using any methods and apparatuses known in the art. In yet another embodiment, the method further comprises drying the pressed waste material using any methods and apparatuses known in the art.

Figure 16:
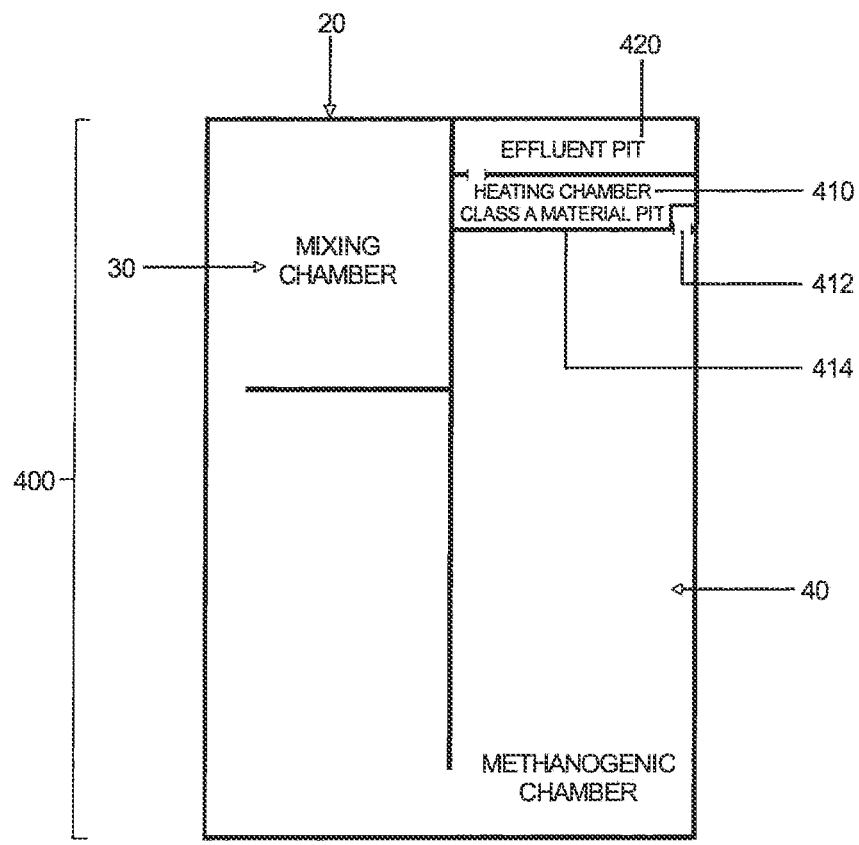
FIG. 16 is a schematic of an alternative waste processing system that can be used to produce biosolids with fecal conform densities less than 1,000 Most Probable Number (MPN) per gram total solids (dry weight density).

A system 400 embodying another aspect of the invention is illustrated in FIG. 16. FIG. 16 shows an anaerobic digester using the basic principles and operating structures discussed above (see FIGS. 1-14) with additional elements that can be used to generate Class A biosolids. The system 400 is described in terms of producing Class A biosolids using waste processing system 10 as described above, but can also be used with other types of anaerobic digesters. The recirculation system of the waste processing system 10 and the system 400 may be employed with other anaerobic digester to produce Class A biosolids.

FIG. 16 shows schematically a system 400 used to produce Class A biosolids from waste material. Components having the same function as in system 10 have like numerals. The system 400 comprises the digester enclosure 20 that includes four major sections: a mixing chamber 30, a digester 40 (also referred to as a "methanogenic chamber"), a heating pit 410 (also referred to as a heating chamber) and an effluent pit 420. The digester enclosure 20 is arranged such that a relatively large digester 40 may be built in relatively small space. Unless stated otherwise, components and elements within the digester enclosure 20, the mixing chamber 30 and the digester 40 are designed and function as described above.

The anaerobically digested waste material plug-flows through an opening 412 in the wall 414 of the methanogenic chamber 40 and into the heating pit 410, where the anaerobically digested material is heated to a temperature sufficient to produce Class A biosolids.

The heating pit 410 can be made of various material including but not limited to plastic, glass and metal. Specific examples of such materials include but are not limited to PVC, polyethylene, polypropylene, methacrylic or acrylic plastic, fiber glass reinforced plastic (FRP), iron or stainless steel.

The heating pit 410 can heat material to any desired temperature including but not limited to 140° F., 141° F., 142° F., 143° F., 144° F., 145° F., 145° F., 147° F., 148° F., 149° F., 150° F., 151° F., 152° F., 153° F., 154° F., 155° F., 156° F., 157° F., 158° F., 159° F., 160° F., 160-170° F., 170-180° F., 180-185° F., 185-190° F., and greater than 190° F. The digested waste material can be heated to a temperature from 135° F. to 180° F.

The heating pit 410 can be designed in any size suitable for the particular location and quantities of waste material, and can have any suitable dimensions including but not limited to 26-40 feet in width and 6-12 feet in length.

The heating pit 410 can be designed to store waste material in any amount including but not limited to 1, 2, 3, 4, 5, 6, 7, 8, 9, 10, 10-20, 20-24, and 24-30, and greater than 30 days of waste material.

In one embodiment, the waste material within the heating pit 410 will be heated and mixed perpendicular to the horizontal plug flow directions. Waste material can be heated by heating pipes along a wall in the heating pit 410 such that convective forces cause the heated waste material to rise near the wall. At the same time, waste material near the relatively cooler outer wall falls under convective forces. Engine exhaust air from the co-gen engines can be injected at the bottom, thereby allowing for efficient mixing via air lift mixing. A draft wall can be used to direct the hydraulic flow-movement and produce a corkscrew-like flow path for the waste material at the bottom of the heating pit. The heating pipes may include jet nozzles, a gas diffuser or a liquid diffuser to dispense heated gas, engine exhaust gas, recycled biogas, or a liquid into the waste material in the heating pit. The heating device induces the waste material to move in a cork-screw like fashion.

In another embodiment, the system 400 may include a heating device for heating the waste material as it flows through the heating pit 410. In one embodiment, the heating device includes one or more heating pipes arranged along one or more than one wall or passageway or a combination thereof of the heating pit 410 or other component of the system 400. The heating device enhances convection and facilitates the corkscrew-like path of the waste material in the heating pit. In addition, gas can be used to facilitate the corks-screw-like flow path of the waste material in the heating pit.

The digester heating pipes locally heat the sludge using, for example, hot water, exhaust, gas, or biogas causing the heated mixed sludge to rise under convective forces. The convective forces cause the heated sludge to rise near the wall of the heating pit 410. At the same time, sludge near the relatively cooler outer wall falls under convective forces. As a result, the convective forces cause the sludge to follow a circular flow path. Likewise, the convective forces cause the sludge to follow a circular flow path downward along the outer wall, resulting in a combined corkscrew-like flow path for the sludge. The heating pipes may include jet nozzles to dispense water or gas into the sludge. In another embodiment, hot gas injection jets using heated gases from the output of the engine (not shown) replace the hot water digester heating pipes as a heating and current-generating source. The injection of hot gases circulates the sludge through both natural and forced convection. A similar cork-screw-like flow path is thereby developed in the digester 40.

In another embodiment, efficient mixing in heating pit 410 is obtained using the exhaust from the co-gen engines and provides a novel and unexpected use of the exhaust. The exhaust from the co-gen engines is about 450° F., and in many instances, is wasted to the ambient air. This embodiment of the invention provides an efficient use of this exhaust. No additional energy is consumed in mixing the waste material within the heating pit. Temperature control of the recycled engine exhaust can be controlled by blending with ambient air utilizing air conductor and variable speed blower.

The waste material, including liquid and solid waste material, will be "plug-flowed" from the heating pit to the effluent pit. The waste material is "plug-flowed" across a separation weir wall 430 and into an effluent pit 420. The effluent pit 420 can be made of various materials including but not limited to plastic, glass and metal. Specific examples of such materials include but are not limited to PVC, polyethylene, polypropylene, methacrylic or acrylic plastic, fiber glass reinforced plastic (FRP), iron or stainless steel.

The effluent pit 420 can be located at any convenient distance from the heating pit including but not limited to adjacent to the heating pit 410. The effluent pit 420 can be designed to store any amount of liquid waste including but not limited to 1, 2, 3, 4, 5, 6, 7, 8, 9, 10, 10-20, 20-30, and greater than 30 days of liquid waste.

The effluent pit 42 can be designed to store any amount of liquid including but not limited to 10,000-25,000; 25,000-50,000; 50,000-100,000; 100,000-200,000; 200,000-400,000; 400,000-500,000; 500,000-1,000,000 and greater than 1 million liters of liquid waste.

The effluent pit 420 will have heat racks in the same configuration as shown in FIG. 13. The heat racks will acquire the surplus heat from the 140° F. waste material and ensure that the heat is effectively used. The entire waste stream can be effectively heated to any suitable temperature including but not limited to 135-140° F., 140-145° F., 145-150° F., 150-155° F., 155-160° F., 160-165° F., 165-170° F., 170-175° F., 175-180° F. and greater than 180° F. The effluent pit comprises heating racks to capture excess energy from the heated waste material.

The material in the effluent pit 420 will be pumped to a separator where in the liquid fraction and solid fraction will be separated. The solids, which can be from 20 to 40% of the waste material, can be used for bedding, fertilizer and fiber-based products. The liquid fraction can be processed for treatment, producing water for stream discharge or animal consumption. In addition, the liquid fraction can be pumped and stored in a lagoon, and used for crop application (see FIG. 15).

In yet another embodiment, the invention relates to an apparatus and method for utilizing waste heat in a waste treatment process. The machines that are used in the waste material processing generate waste heat. This heat may be collected and used to meet the heating demands of the thermophilic phase of the treatment process. Furthermore, heat and electricity generated in excess of that used in the anaerobic digestion process can be used as a power source to meet other energy requirements. Furthermore, waste heat and electricity from the generation step may be used to dry the Class A biosolids to the appropriate level.

Figure 17:
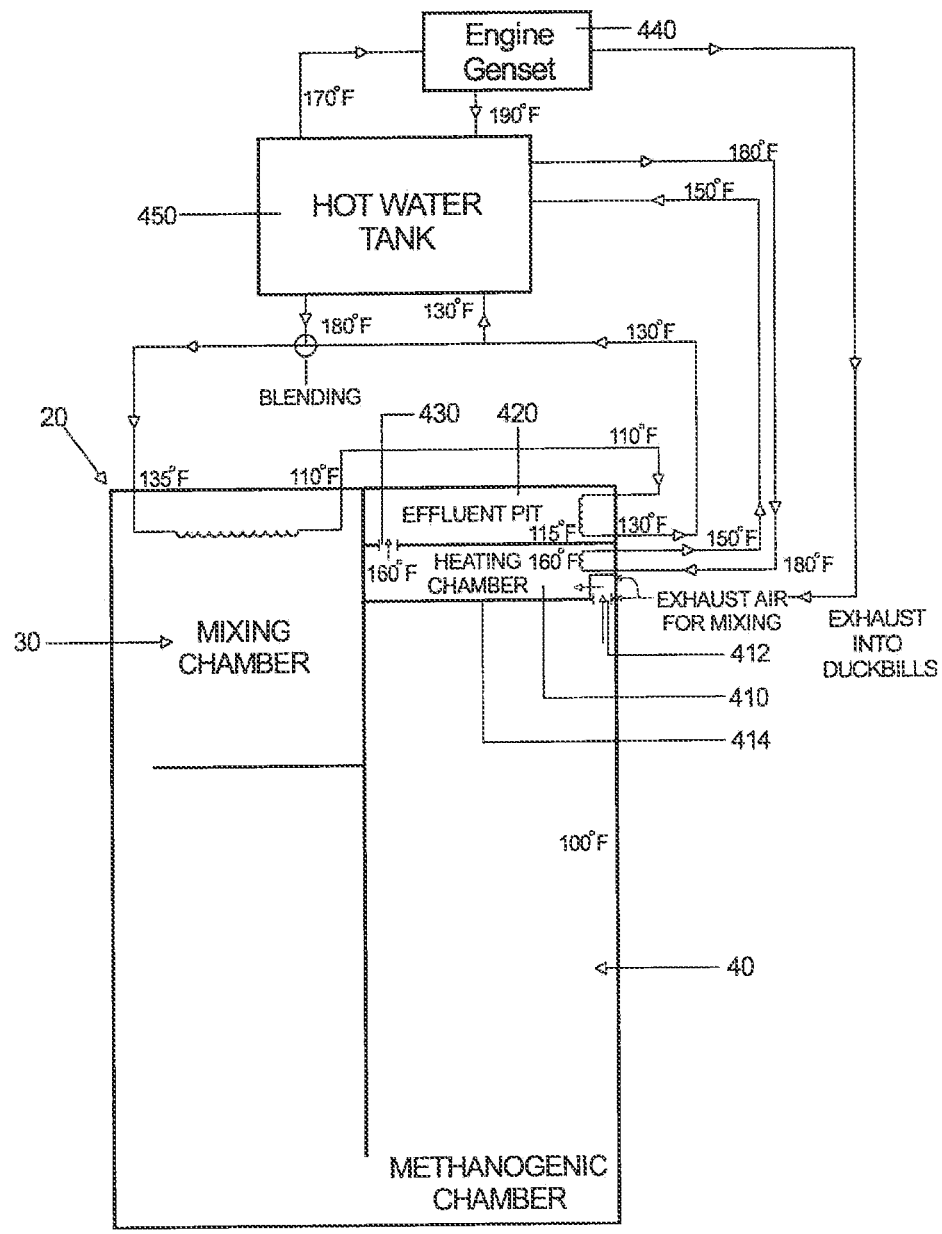
FIG. 17 is a schematic of an alternative waste processing system depicting energy usage and conservation.

FIG. 17 shows one representative example of an energy-efficient anaerobic digestion process that can produce Class A biosolids. A generator 440 supplies energy in the form of waste heat or biogas to a hot water tank 450. Energy (180° F.) from the hot water tank 450 is provided to the mixing chamber 30 of a digester enclosure 20, wherein the mixing chamber 30 contains waste material. In one embodiment, the waste material is heated to about 100° F. in the digester 40. The material can be heated to a mesophilic temperature range of 15-40° C. (77-104° F.) for a thermophilic temperature range of 41-80° C. (113-176° F.).

The waste material is moved into the heating pit 410, wherein the exhaust air from the co-gen engines is used to heat the waste material to a temperature suitable to produce a Class A biosolid, including but not limited to 135-140° F., 140-145° F., 145-150° F., 150-155° F., 155-160° F., 160-165° F., 165-170° F., 170-175° F., 175-180° F., and greater than 180° F. Energy (180° F.) necessary to heat the waste material is also provided by the hot water tank. Energy (150° F.) is returned from the heating pit 410 to the hot water tank 450.

After heating the waste material to a suitable temperature and for a suitable period of time, the waste material, including both solid and liquid waste, is plug-flowed over a separation weir wall 430, wherein the waste is stored in an effluent pit 420 comprising heating racks. The heating racks capture excess energy from the heated waste material and return energy (135° F.) back to the hot water tank. Energy from the hot water tank (170° F.) is then returned to the generator.

In another embodiment, a shell and tube heat exchanger or circular heat exchanger can be used to remove excess energy. The waste material is moved from the effluent pit to a separator, and pumped through a shell and tube or spiral heat exchanger. This type of heat exchanger consists of a shell (a large pressure vessel) with a bundle of tubes inside. One fluid runs through the tubes, and another fluid flows over the tubes (through the shell) to transfer heat between the two fluids. The set of tubes is called a tube bundle, and may be composed by several types of tubes: plain, longitudinally finned, etc. In order to transfer heat efficiently, a large heat transfer area should be used, leading to the use of many tubes. Any type of shell tube heat exchanger can be used including but not limited to a U-tube heat exchanger, straight-tube heat exchanger (one pass tube-side), and a straight-tube heat exchanger (two pass tube-side).

Figure 18:
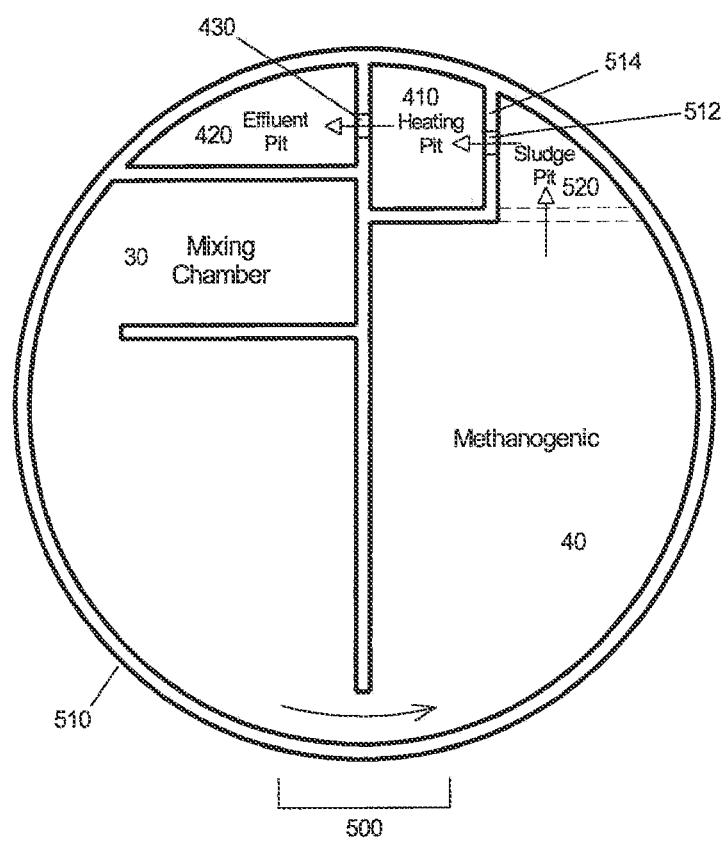
FIG. 18 is a schematic of a circular anaerobic digester that can be used to produce biosolids with fecal coliform densities less than 1,000 Most Probable Number (MPN) per gram total solids (dry weight density).

In yet another embodiment, FIG. 18 shows schematically a circular system 500 used to produce Class A biosolids from waste material. Components having the same function as in system 10 have like numerals. The system 500 comprises a circular digester enclosure 510 that includes five major sections: a mixing chamber 30, a digester 40, a sludge pit 520, a heating pit 410 and an effluent pit 420. The digester enclosure 510 is circular in shape but can be modified into the necessary dimensions and shape to meet space restrictions. Unless stated otherwise, component and elements within the digester enclosure 510, the mixing chamber 30 and the digester 40 work as described above.

The anaerobically digested waste material plug-flows through an opening 512 in the wall 514 and into the heating pit 410, where the anaerobically digested material is heated to a temperature sufficient to produce Class A biosolids as discussed above in detail.

The waste material, including liquid and solid waste material, will be "plug-flowed" across a separation weir wall 430 and into an effluent pit 420. The effluent pit 420 can be made of various materials including but not limited to plastic, glass and metal.

The material in the effluent pit 420 will be pumped to a separator where the liquid fraction and solid fraction will be separated. The solids, which can be 20-40% of the waste material, can be used for bedding, fertilizer and fiber-based products. The liquid fraction can be processed for treatment, producing water for stream discharge or animal consumption. In addition, the liquid fraction can be pumped and stored in a lagoon, and used for crop application (see FIG. 15).

Examples of suitable separators include flotation separators, centrifuges, clarifiers, plate separators, gravity belts, cyclones, membranes, filters, or any number of a variety of solid-liquid separators.

Figure 19:
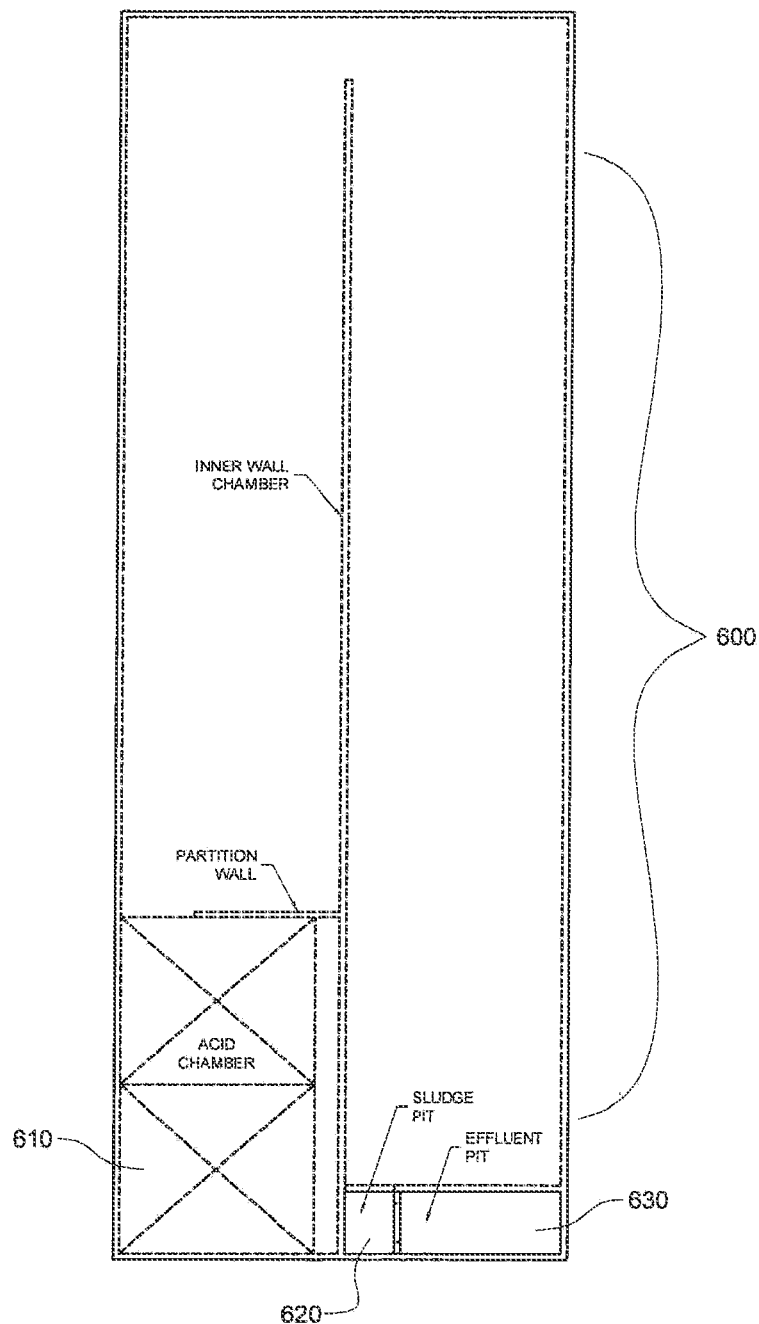
FIG. 19 is a schematic of a single anaerobic digester that can be used with a heating pit to produce Class A biosolids.

FIG. 19 provides a plain view schematic of an anaerobic digester. The system 600 displays an anaerobic digester with an acidic chamber 610, a sludge pit 620, and an effluent pit 630. A heating pit, as discussed above, can be used in conjunction with the system 600 to produce Class A biosolids.

Figure 20:
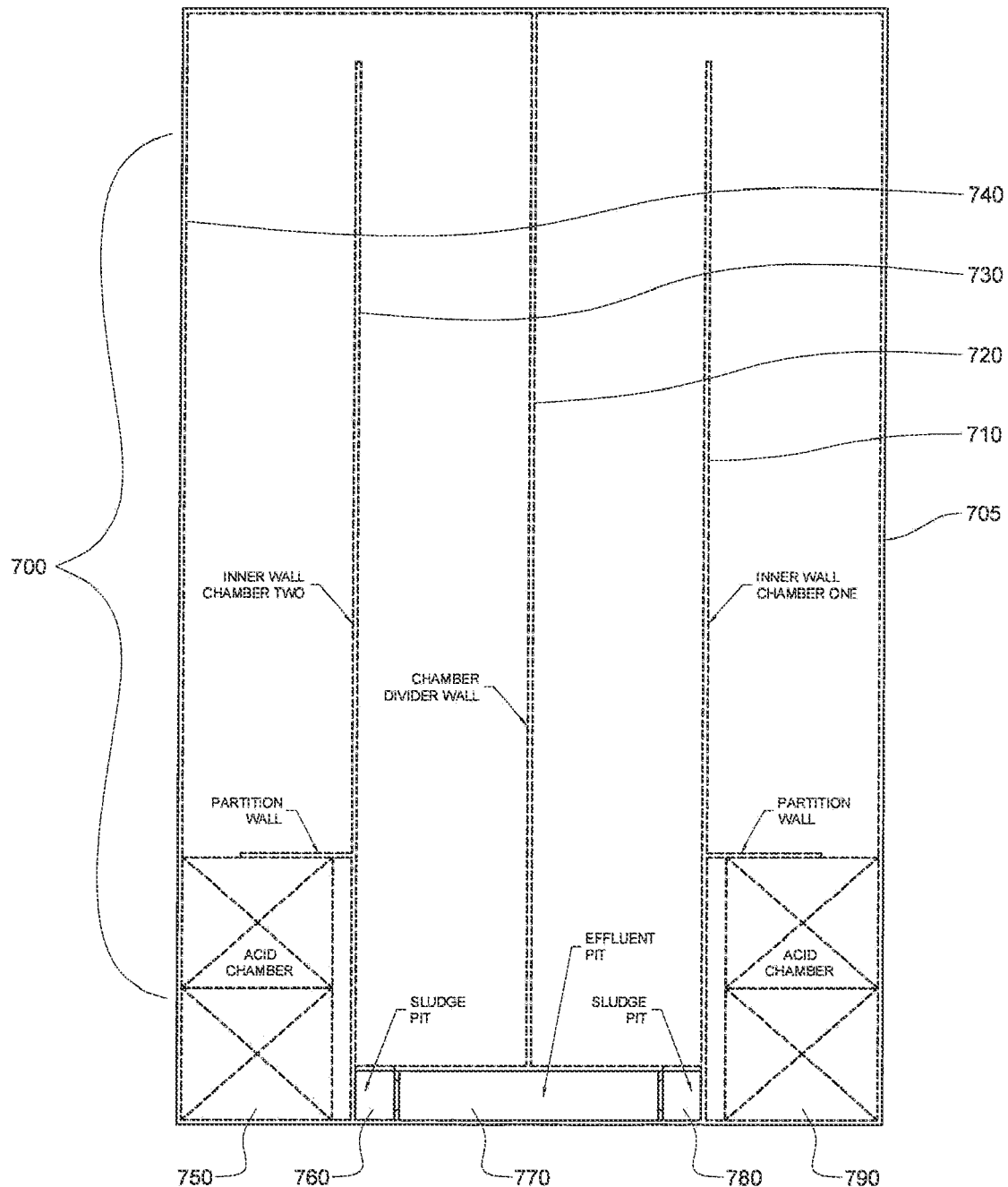
FIG. 20 is a schematic of a double anaerobic digester that can be used with a heating pit to produce Class A biosolids.

FIG. 20 provides a plain view schematic of a double digester. The system 700 displays two anaerobic digesters parallel to one another. The system 700 has a first anaerobic digester comprising an outer wall chamber one 705, and inner wall chamber one 710. Anaerobic digester one has an acidic chamber 790 and a sludge pit 780. An effluent pit 770 is adjacent to sludge pit 780.

The system 700 has a chamber divider wall 720, which partitions anaerobic digester one from anaerobic digester two. The effluent pit 770 is shared between anaerobic digester one and anaerobic digester two. The use of a single effluent pit provides efficient use of resources and cost savings to the end user.

The system 700 has a second anaerobic digester comprising an inner wall 730 and an outer wall 740. The second anaerobic digester has an acidic chamber 750, a sludge pit 760, and an effluent pit 770.

A first heating pit can be configured between the sludge pit 780 and effluent pit 770, and a second heating pit can be positioned between sludge pit 760 and effluent pit 770.

FIG. 20 displays two parallel digesters, however, any number of digesters can be configured using the principles outlined above including but not limited to 2, 3, 4, 5, 6, 7, 8, 9, 10, and more than 10.

Figure 21:
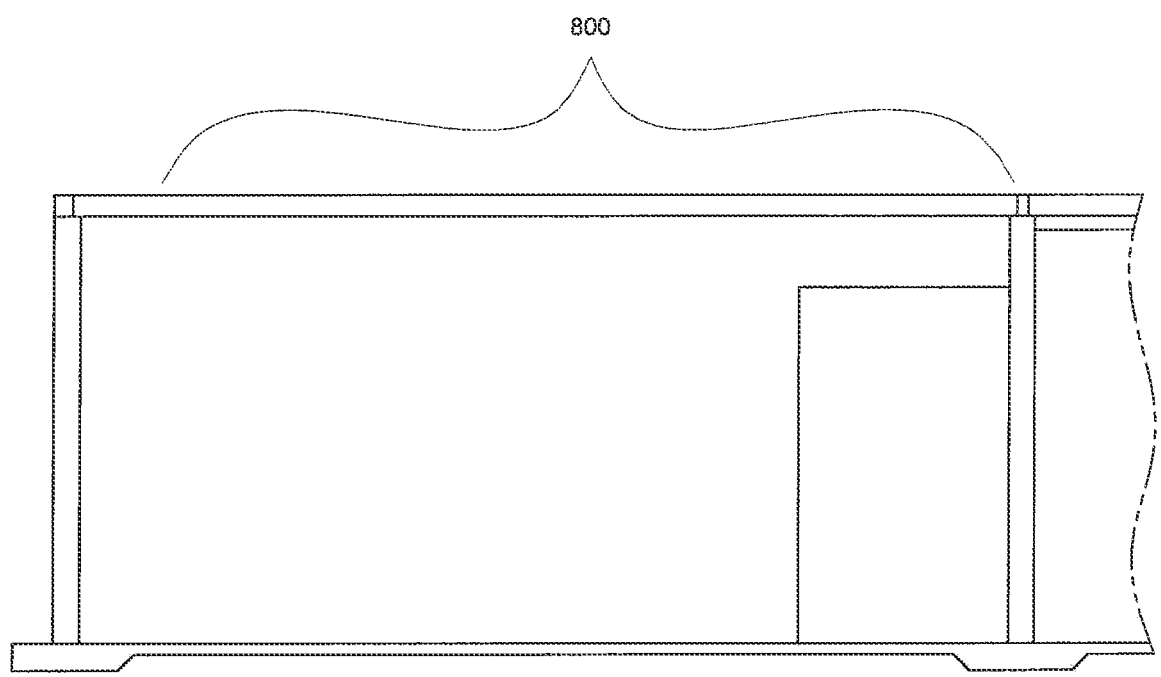
FIG. 21 is a schematic of a gas wall.
Figure 22:
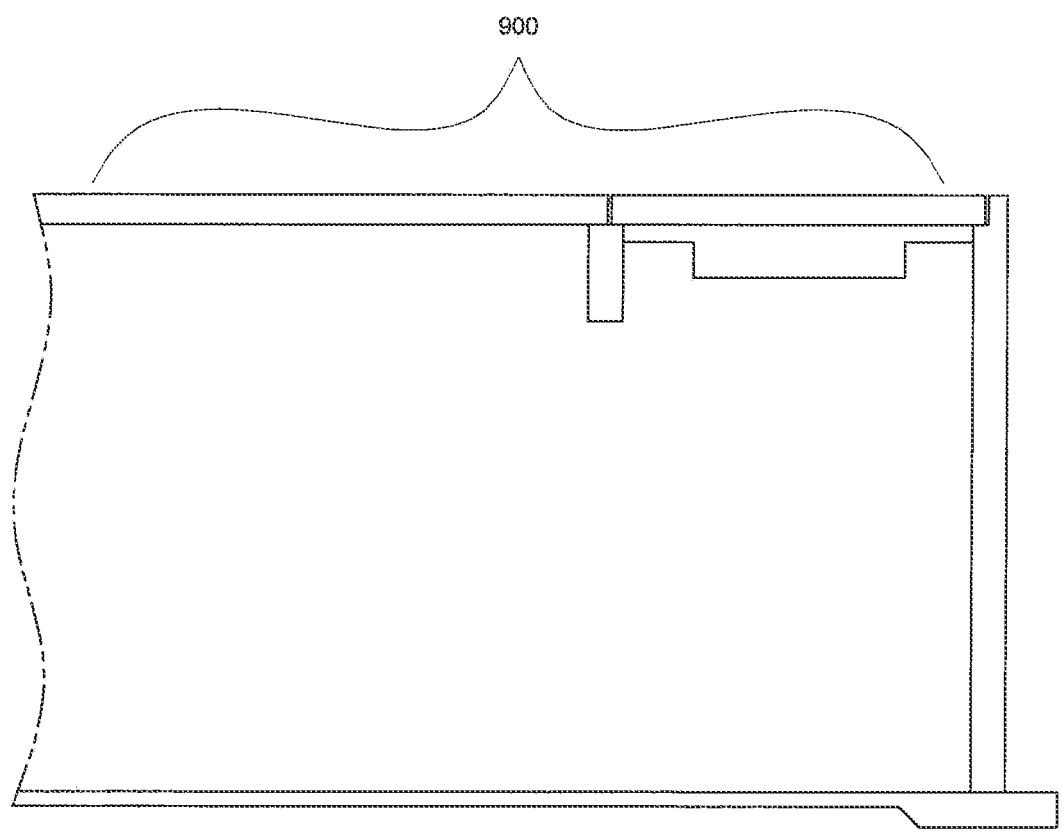
FIG. 22 is a schematic of a gas wall and weir wall.

FIG. 21 provides a schematic of a gas wall 800. FIG. 22 provides a schematic of a gas wall and weir wall 900.

In one embodiment, disclosed herein is a waste processing system comprising: a closed container comprising an anaerobic digester with a first passage and a second passage separated by a center wall, wherein the digester has outside walls, and further wherein the center wall and outside walls are substantially planar and vertical; and a heating pit that is adjacent to the anaerobic digester and shares a wall with the anaerobic digester, wherein the heating pit comprises a first heating device with heating pipes.

In yet another embodiment, disclosed herein is a waste processing system comprising: a closed container comprising an anaerobic digester with a first passage and a second passage separated by a center wall, wherein the digester has outside walls, and further wherein the center wall and outside walls are substantially planar and vertical; a heating pit that is adjacent to the anaerobic digester and shares a common wall with the anaerobic digester, wherein the heating pit comprises a first heating device to move waste material in a cork-screw-like fashion; and an effluent pit that is adjacent to and shares a common wall with the heating pit, and wherein the effluent pit comprises heating racks to capture excess heat.

In another embodiment, the first heating device includes a conduit having at least one gas outlet positioned to promote upward movement of the heated waste material utilizing a gas, including but not limited to recycled biogas. In yet another embodiment, the first heating device contains a heating medium.

In still yet another embodiment, the system comprises a second heating device positioned in at least a portion of one of the first passage and the second passage to heat the waste material that comes in contact with the heating device to cause thermal mixing of the waste. In another embodiment, the second heating device is positioned adjacent a wall. In yet another embodiment, the second heating device is positioned adjacent the divider of the digester. In another embodiment, the second heating device includes a pipe containing a heating medium.

In one embodiment, the heating medium comprises water. In still another embodiment, the heating medium comprises a gas.

In another embodiment, the heating pit 410 has opposing first and second sidewalls 411, 413 an inlet wall 414 and an outlet wall 416. The heating pit 410 also has bottom wall 417 and an optional top wall 418. The top wall 418 may be removable and the system is operable with or without the top wall 418. The heating pit walls define an interior. The heating pit 410, and/or the walls thereof, may be transparent, translucent, or opaque. The heating pit walls may be made of glass, polymeric material, metal, concrete, insulative material, and any combination thereof. The walls of the heating pit may be flexible or rigid. The heating pit 410 can be water-tight. One, some, or all of the container inner surfaces may include a reflective material, a light source, a thermal element, and any combination thereof. The heating pit may comprise a weir wall.

In another embodiment, the effluent pit 420 has opposing first and second sidewalls 421, 422, and inlet wall 423 and an outlet wall 424. The effluent pit 420 also has a bottom wall 425 and an optional top wall 426. The top wall 426 may be removable and the system is operable with or without the top wall 426. The effluent pit walls define an interior. The effluent pit 420, and/or the walls thereof, may be transparent, translucent, or opaque. The effluent pit walls may be made of glass, polymeric material, metal, concrete, insulative material, and any combination thereof. The walls of the effluent pit may be flexible or rigid. The effluent pit 410 can be water-tight. One, some, or all of the container inner surfaces may include a reflective material, a light source, a thermal element, and any combination thereof. The effluent pit may comprise a weir wall.

In another embodiment, the waste processing system may comprise a sludge pit as shown in FIG. 18. A sludge pit can be used with waste processing systems that are of any shape, and is not limited to circular anaerobic digesters.

In another embodiment, the sludge pit has opposing first and second sidewalls, an inlet wall, and an outlet wall. The sludge pit also has a bottom wall and an optional top wall. The top wall may be removable and the system is operable with or without the top wall. The sludge pit walls define an interior. The sludge pit, and/or the walls thereof, may be transparent, translucent, or opaque. The sludge pit walls may be made of glass, polymeric material, metal, concrete, insulative material, and any combination thereof. The walls of the sludge pit may be flexible or rigid. The sludge pit can be water-tight. One, some, or all of the container inner surfaces may include a reflective material, a light source, a thermal element, and any combination thereof. The sludge pit may comprise a weir wall.

The invention allows for the production of Class A biosolids in an energy efficient manner. The system captures and recycles energy from several systems such as biogas generated during anaerobic digestion and exhaust waste heat from the co-gen engines. The system allows for the heating pit to be designed to allow for one days storage of waste material, which can not be obtained with "totally mixed" digesters. In addition, the system allows for the waste material to be heated to at least 140° F. in an energy efficient manner, which exceeds the recommended temperature. The waste material can be heated to any suitable temperature including but not limited to 135-140, 140-145, 145-150, 150-155, 155-160, 160-165, 165-170, 170-175, 175-180 and greater than 180° F. The above advantages are significant and provide novel uses of energy that typically are wasted to the environment.

Class A biosolids are beneficial soil amendment. Land application of Class A biosolids recycles soil-enhancing constituents such as plant nutrients and organic matter. The main fertilizer benefits are through the supply of nitrogen ($N_2$) and phosphorus (P). In addition, biosolids also ensure against unforeseen nutrient shortages by supplying essential plant nutrients (e.g., sulfur (S), manganese (Mn), zinc (Zu), copper (Cu), iron (Fe), molybdenum (Mo), and boron (B). Methods and apparatuses that convert waste material into Class A biosolids in an energy efficient manner offer tremendous advantages. In the absence of the teaching disclosed herein, Class A biosolids required sufficient energy resources, which resulted in very little use of Class A biosolids. The invention described herein removes these high energy requirements.

Furthermore, Class A biosolids can be used as cow bedding and should further reduce the number of infections observed within the herd. In addition, Class A biosolids can be re-circulated back to the herd of animals. The Class A biosolids provide a rich source of dietary requirements.

It is specifically intended that the invention not be limited to the embodiments and illustrations contained herein, but include modified forms of those embodiments including portions of the embodiments and combinations of elements of different embodiments as come within the scope of the following claims.

Although specific embodiments have been illustrated and described herein, it will be appreciated by those of ordinary skill in the art that any arrangement that is calculated to achieve the same purpose may be substituted for the specific embodiments shown. This application is intended to cover any adaptations or variations that operate according to the principles of the invention as described. Therefore, it is intended that this invention be limited only by the claims and the equivalents thereof. The disclosures of patents, references and publications cited in the application are incorporated by reference herein.

What is claimed is:

1. A waste processing system comprising: a closed container having a mixing chamber configured to receive waste material, wherein said mixing chamber comprises heating coils configured to heat the waste material to at least 100° F.; a methanogenic chamber configured for digesting waste material; a sludge pit configured to receive waste material from the methanogenic chamber; a heating pit comprising an inlet wall and an outlet wall, wherein the inlet wall separates the heating pit from the sludge pit and has an opening configured to receive waste material from the sludge pit, and further wherein the heating pit includes a heating device configured to heat digested waste material to a temperature from 140° F. to 180° F.; and an effluent pit sharing the outlet wall with the heating pit, wherein the outlet wall has an opening to receive heated waste material from the heating pit.

2. The system of claim 1 further comprising a hot water tank to supply heat to the methanogenic chamber.

3. The system of claim 1 further comprising an engine, wherein exhaust air from the engine can be supplied to the heating pit for mixing of the waste material.

4. The system of claim 1, wherein the heating device in the heating pit comprises a conduit having at least one gas outlet positioned to promote upward movement of the heated waste material utilizing recycled biogas.

5. The system of claim 1, wherein the inlet and outlet walls of the heating pit are configured to allow storage of one day of waste material.

6. The system of claim 1, wherein the first heating device contains a heating medium.

7. The system of claim 1, wherein the methanogenic chamber has a center wall that divides the methanogenic chamber into a first passage and a second passage, and further wherein a second heating device is positioned in at least a portion of one of the first passage and the second passage to heat the waste material that comes in contact with the second heating device.

8. The system of claim 7, wherein the second heating device is positioned adjacent the center wall of the methanogenic chamber.

9. The system of claim 7, wherein the second heating device includes a pipe containing a heating medium.

10. The system of claim 9, wherein the heating medium comprises water.

11. The system of claim 9, wherein the heating medium comprises a gas.

* * * * *